United States Patent
Walter et al.

(10) Patent No.: US 8,357,635 B2
(45) Date of Patent: Jan. 22, 2013

(54) MICROBIOCIDES

(75) Inventors: Harald Walter, Stein (CH); Daniel Stierli, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 0 days.

(21) Appl. No.: 13/502,368

(22) PCT Filed: Oct. 14, 2010

(86) PCT No.: PCT/EP2010/065371
§ 371 (c)(1),
(2), (4) Date: Apr. 16, 2012

(87) PCT Pub. No.: WO2011/045355
PCT Pub. Date: Apr. 21, 2011

(65) Prior Publication Data
US 2012/0202867 A1   Aug. 9, 2012

(30) Foreign Application Priority Data
Oct. 16, 2009 (EP) ..................... 09173257

(51) Int. Cl.
*A01N 43/56* (2006.01)
*C07D 231/10* (2006.01)
(52) U.S. Cl. ................... 504/280; 548/374.1
(58) Field of Classification Search ................ 504/280; 548/374.1
See application file for complete search history.

(56) References Cited

U.S. PATENT DOCUMENTS

| | | | |
|---|---|---|---|
| 3,541,106 | A | 11/1970 | Krenzer et al. |
| 6,291,520 | B1 | 9/2001 | Ikeda et al. |

FOREIGN PATENT DOCUMENTS

| | | |
|---|---|---|
| EP | 0436199 | 7/1991 |
| WO | 0159584 | 10/1985 |
| WO | 2007134799 | 11/2007 |

OTHER PUBLICATIONS

Wu, Pei-Lin et al: "Homodienyl [1,5]-Hydrogen Shift of cis- and trans-N-Acyl-2-alkylcyclopropylimines", Journal of Organic Chemistry, 62(5), pp. 1532-1535, 1997.

*Primary Examiner* — Samantha Shterengarts
(74) *Attorney, Agent, or Firm* — R. Kody Jones

(57) ABSTRACT

Compounds of formula (I), in which the substituents are as defined in claim 1, are suitable for use as microbiocides.

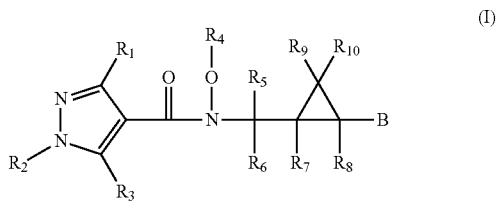

12 Claims, No Drawings

MICROBIOCIDES

This application is a 371 of International Application No. PCT/EP2010/065371 filed Oct. 14, 2010, which claims priority to EP 09173257.8 filed Oct. 16, 2009, the contents of which are incorporated herein by reference.

The present invention relates to novel microbiocidally active, in particular fungicidally active, carboxamides. It further relates to intermediates used in the preparation of these compounds, to compositions which comprise these compounds and to their use in agriculture or horticulture for controlling or preventing infestation of plants by phytopathogenic microorganisms, preferably fungi.

Fungicidally active carboxamides are described in WO 2007/134799.

It has been found that novel carboxamides with a specific substitution pattern have microbiocidal activity.

The present invention accordingly relates to N-alkoxycarboxamides of formula I

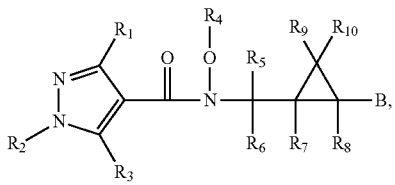

(I)

wherein
$R_1$ is $C_1$-$C_4$alkyl or $C_1$-$C_4$haloalkyl;
$R_2$ is $C_1$-$C_4$alkyl;
$R_3$ is hydrogen or halogen;
$R_4$ is hydrogen, $C_1$-$C_4$alkyl or $C_1$-$C_4$halogenalkyl;
$R_5$ and $R_6$ are, independently from each other, hydrogen, halogen, $C_1$-$C_4$alkyl or $C_1$-$C_4$haloalkyl;
$R_7$, $R_8$, $R_9$ and $R_{10}$ are, independently from each other, hydrogen, halogen, $C_1$-$C_6$alkyl, $C_2$-$C_6$alkenyl, $C_3$-$C_6$alkinyl or $C_1$-$C_4$alkoxy;
B is a phenyl or thienyl group, which groups are substituted by $R_{11}$, $R_{12}$ and $R_{13}$;
$R_{11}$, $R_{12}$ and $R_{13}$ are, independently from each other, hydrogen, halogen, $C_1$-$C_6$alkyl, $C_3$-$C_6$alkinyl, $C_1$-$C_4$alkoxy, $C_3$-$C_6$cycloalkyl-$C_3$-$C_6$alkinyl, halophenoxy, halophenyl-$C_3$-$C_6$alkinyl, $C_1$-$C_6$haloalkyl, $C_1$-$C_6$haloalkoxy, or $C_2$-$C_6$haloalkenyloxy; and agrochemically acceptable salts/isomers/structural isomers/stereoisomers/diastereoisomers/enantiomers/tautomers and N-oxides of those compounds.

The compounds of formula I occur in at least two different isomeric forms: $I_I$ (cis) and $I_{II}$ (trans):

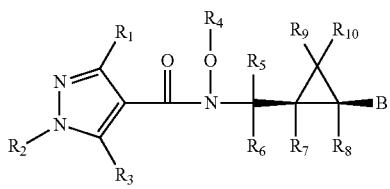

$I_I$

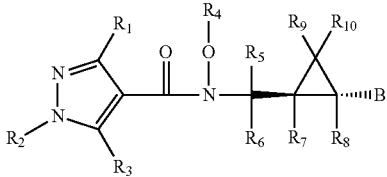

$I_{II}$

The invention covers all agrochemically acceptable salts/isomers/structural isomers/stereoisomers/diastereoisomers/enantiomers/tautomers and N-oxides of those compounds.

The alkyl groups occurring in the definitions of the substituents can be straight-chain or branched and are, for example, methyl, ethyl, n-propyl, n-butyl, n-pentyl, n-hexyl, iso-propyl, n-butyl, sec-butyl, iso-butyl or tert-butyl. Alkoxy, alkenyl and alkynyl radicals are derived from the alkyl radicals mentioned. The alkenyl and alkynyl groups can be mono- or di-unsaturated. The cycloalkyl groups occurring in the definitions of the substituents are, for example, cyclopropyl, cyclobutyl, cyclopentyl or cyclohexyl. Halogen is generally fluorine, chlorine, bromine or iodine, preferably fluorine, bromine or chlorine. This also applies, correspondingly, to halogen in combination with other meanings, such as halogenalkyl or halogenalkoxy. Haloalkyl groups preferably have a chain length of from 1 to 4 carbon atoms. Halonalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl. Alkoxy is, for example, methoxy, ethoxy, propoxy, i-propoxy, n-butoxy, isobutoxy, sec-butoxy and tert-butoxy; preferably methoxy and ethoxy. Halogenalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy.

In a preferred group of compounds of formula I, B is $B_1$

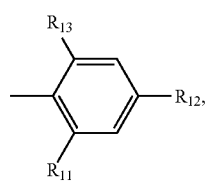

($B_1$)

wherein
$R_{11}$, $R_{12}$ and $R_{13}$ are, independently from each other, hydrogen, halogen or $C_1$-$C_6$alkyl;
preferably hydrogen or halogen; most preferably at least one of $R_{11}$, $R_{12}$ and $R_{13}$ is halogen;
or B is $B_2$

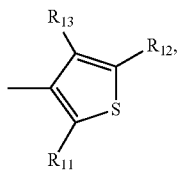

(B₂)

wherein
$R_{11}$, $R_{12}$ and $R_{13}$ are, independently from each other, hydrogen, halogen or $C_1$-$C_6$alkyl;
preferably hydrogen or halogen; most preferably at least one of $R_{11}$, $R_{12}$ and $R_{13}$ is halogen;
or B is $B_3$

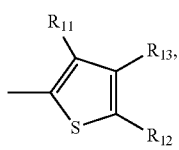

(B₃)

wherein
$R_{11}$, $R_{12}$ and $R_{13}$ are, independently from each other, hydrogen, halogen or $C_1$-$C_6$alkyl;
preferably hydrogen or halogen; most preferably at least one of $R_{11}$, $R_{12}$ and $R_{13}$ is halogen;

Especially preferred are compounds of formula I, wherein
$R_1$ is $C_1$-$C_4$haloalkyl;
$R_2$ is $C_1$-$C_4$ alkyl;
$R_3$ is hydrogen;
$R_4$ is $C_1$-$C_4$alkyl;
$R_5$ is hydrogen or $C_1$-$C_4$alkyl;
$R_6$ is hydrogen;
$R_7$ is hydrogen, $C_1$-$C_4$alkyl or halogen;
$R_8$ is hydrogen, $C_1$-$C_4$alkyl or halogen;
$R_9$ is hydrogen, $C_1$-$C_4$alkyl or halogen;
$R_{10}$ is hydrogen, $C_1$-$C_4$alkyl or halogen; and
$R_{11}$, $R_{12}$ and $R_{13}$ are, independently from each other, hydrogen or halogen.
In preferred compounds from this group, $R_5$ is methyl.
In preferred compounds from this group, at least one of $R_{11}$, $R_{12}$ and $R_{13}$ is halogen.
In preferred compounds from this group, $B_1$, $B_2$ and $B_3$ have the preferred meanings as mentioned above.

In further especially preferred compounds of formula I,
$R_1$ is difluoromethyl;
$R_2$ is methyl;
$R_3$ is hydrogen;
$R_4$ is methyl;
$R_5$ is hydrogen or methyl;
$R_6$ is hydrogen;
$R_7$ is hydrogen, methoxy or chloro; and
$R_8$, $R_9$ and $R_{10}$ are hydrogen;

In further preferred compounds of formula I, independently from each other,
a) $R_1$ is difluoromethyl, trifluoromethyl or methyl,
b) $R_2$ is methyl;
c) $R_3$ is hydrogen or fluoro;
d) $R_4$ is hydrogen, methyl or ethyl; preferably methyl;
e) $R_5$ is hydrogen, methyl or ethyl; and
g) $R_6$ is hydrogen;

Particularly preferred compounds of formula I are those, wherein
$R_1$ is difluoromethyl or trifluoromethyl;
$R_2$ is methyl;
$R_3$ is hydrogen;
$R_4$ is methyl;
$R_5$ is hydrogen, methyl or ethyl; and
$R_6$, $R_7$, $R_8$, $R_9$ and $R_{10}$ are hydrogen.

In outstanding compounds of formula I,
$R_1$ is $C_1$-$C_4$haloalkyl;
$R_2$ is $C_1$-$C_4$alkyl;
$R_3$ is hydrogen;
$R_4$ is $C_1$-$C_4$alkyl;
$R_5$ is $C_1$-$C_4$alkyl;
$R_6$, $R_7$, $R_8$, $R_9$ and $R_{10}$ are hydrogen;
B is a phenyl or thienyl group, which groups are substituted by $R_{11}$, $R_{12}$ and $R_{13}$; and
$R_{11}$, $R_{12}$ and $R_{13}$ are, independently from each other, hydrogen or halogen.

In said outstanding compounds of formula I, B is preferably $B_1$, $B_2$ or $B_3$, in particular $B_1$.

Compounds of formula I may be prepared by reacting a compound of formula II

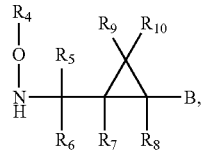

(II)

wherein $R_4$, $R_5$, $R_6$, $R_7$, $R_8$, $R_9$, $R_{10}$, and B are as defined under formula I; with a compound of formula III

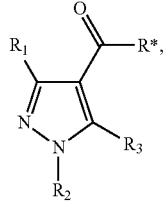

(III)

in which $R_1$, $R_2$ and $R_3$ are as defined under formula I, and R* is halogen, hydroxy or $C_{1-6}$ alkoxy, preferably chloro.

The reactions to give compounds of formula I are advantageously carried out in aprotic inert organic solvents. Such solvents are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitriles such as acetonitrile or propionitrile, amides such as N,N-dimethylformamide, diethylformamide or N-methylpyrrolidinone. The reaction temperatures are advantageously between −20° C. and +120° C. In general, the reactions are slightly exothermic and, as a rule, they can be carried out at ambient temperature. To shorten the reaction time, or else to start the reaction, the mixture may be heated briefly to the boiling point of the reaction mixture. The reaction times can also be shortened by adding a few drops of base as reaction catalyst. Suitable bases are, in particular, tertiary amines such as trimethylamine, triethylamine, quinuclidine, 1,4-diazabicyclo[2.2.2]octane, 1,5-diazabicyclo[4.3.0]non-5-ene or 1,5-diazabicyclo[5.4.0]undec-7-ene. However, inorganic bases such as hydrides, e.g. sodium hydride or calcium hydride, hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases. The bases can be used as such or else with catalytic amounts of a phase-transfer catalyst, for example a crown ether, in particular 18-crown-6, or a tetraalkylammonium salt.

When R* is hydroxy, a coupling agent, such as benzotriazol-1-yloxytris(dimethylamino) phosphoniumhexafluorophosphate, bis-(2-oxo-3-oxazolidinyl)-phosphinic acid chloride (BOP-Cl), N,N'-dicyclohexylcarbodiimide (DCC) or 1,1'-carbonyl-diimidazole (CD), may be used.

The intermediates of formula II

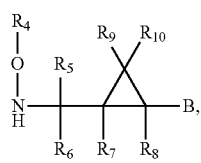
(II)

wherein $R_4$, $R_5$, $R_6$, $R_7$, $R_8$, $R_9$, $R_{10}$, and B are as defined under formula I, preferably wherein $R_4$ is $C_1$-$C_4$alkyl; are novel and were developed specifically for the preparation of the compounds of the formula I. Accordingly, these intermediates of formula II also form a part of the subject-matter of the present invention.

The preferred substituent definitions for the compounds of formula I are also valid for the compound of formula II. Thus, preferred compounds of formula II are those, wherein B is $B_1$

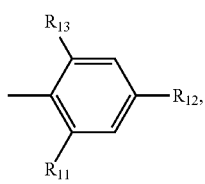
($B_1$)

wherein
$R_{11}$, $R_{12}$ and $R_{13}$ are, independently from each other, hydrogen, halogen or $C_1$-$C_6$alkyl;
or B is $B_2$

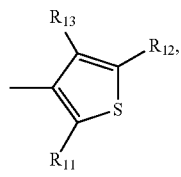
($B_2$)

wherein
$R_{11}$, $R_{12}$ and $R_{13}$ are, independently from each other, hydrogen, halogen or $C_1$-$C_6$alkyl;
or B is $B_3$

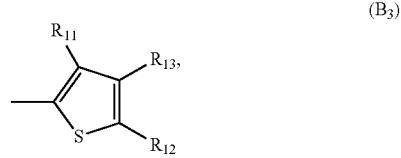
($B_3$)

wherein
$R_{11}$, $R_{12}$ and $R_{13}$ are, independently from each other, hydrogen, halogen or $C_1$-$C_6$alkyl;
Especially preferred are compounds of formula II, wherein
$R_4$ is $C_1$-$C_4$alkyl;
$R_5$ is hydrogen or $C_1$-$C_4$alkyl;
$R_6$ is hydrogen;
$R_7$ is hydrogen, $C_1$-$C_4$alkyl or halogen;
$R_8$ is hydrogen, $C_1$-$C_4$alkyl or halogen;
$R_9$ is hydrogen, $C_1$-$C_4$alkyl or halogen; and
$R_{10}$ is hydrogen, $C_1$-$C_4$alkyl or halogen. In preferred compounds from this group, $R_5$ is methyl.

In further especially preferred compounds of formula $I_1$,
$R_4$ is methyl;
$R_5$ is hydrogen or methyl;
$R_6$ is hydrogen;
$R_7$ is hydrogen, methoxy or chloro; and
$R_8$, $R_9$ and $R_{10}$ are hydrogen.

In further preferred compounds of formula II, independently from each other,
a) $R_4$ is hydrogen, methyl or ethyl; preferably methyl;
b) $R_5$ is hydrogen, methyl or ethyl; and
c) $R_6$ is hydrogen;
Particularly preferred compounds of formula II are those, wherein
$R_4$ is methyl;
$R_5$ is hydrogen, methyl or ethyl; and
$R_6$, $R_7$, $R_8$, $R_9$ and $R_{10}$ are hydrogen.

In outstanding compounds of formula II,
$R_4$ is $C_1$-$C_4$alkyl;
$R_5$ is $C_1$-$C_4$alkyl;
$R_6$, $R_7$, $R_8$, $R_9$ and $R_{10}$ are hydrogen;
B is a phenyl or thienyl group, which groups are substituted by $R_{11}$, $R_{12}$ and $R_{13}$; and
$R_{11}$, $R_{12}$ and $R_{13}$ are, independently from each other, hydrogen or halogen.

Intermediates of formula IIA

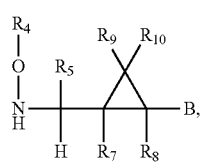
(IIA)

wherein $R_4$, $R_5$, $R_7$, $R_8$, $R_9$, $R_{10}$ and B are as defined under formula I, may be prepared as described in reaction scheme 1.

Scheme 1:

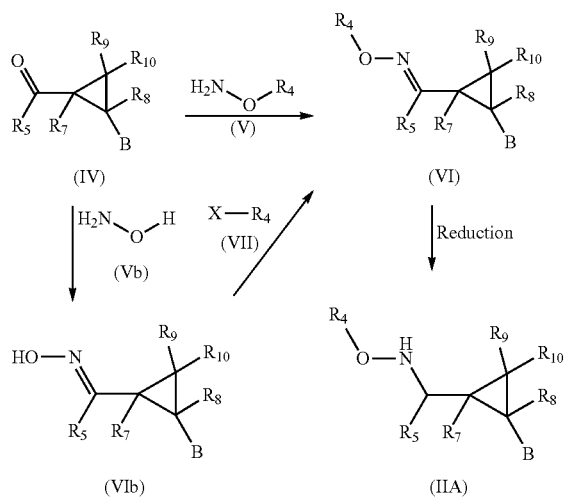

Oxime ether derivatives of formula VI, in which and $R_4$, $R_5$, $R_7$, $R_8$, $R_9$, $R_{19}$ and B are as defined under formula I may be prepared by oximation of ketones or aldehydes of formula IV with O-alkyl hydroxylamine derivatives of formula V or a salt thereof.

Suitable solvents carrying out the oximation step are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitriles such as acetonitrile or propionitrile, amides such as N,N-dimethylformamide, diethylformamide, N-methylpyrrolidinone, alcohols such as methanol, ethanol, n-propanol, i-propanol, n-butanol, sec.butanol water or mixtures. The reaction temperatures are advantageously between –20° C. and +120° C. In general, the reactions can be carried out at ambient temperature. Suitable bases are, in particular pyridine, tertiary amines such as trimethylamine, triethylamine, huenig base, quinuclidine, 1,4-diazabicyclo[2.2.2]octane, 1,5-diazabicyclo[4.3.0]non-5-ene or 1,5-diazabicyclo[5.4.0]undec-7-ene. However, inorganic bases such as hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases.

Alternatively, oxime ether derivatives of formula VI may be prepared by O-alkylation of oxime derivatives of formula VIb with a compound of formula VII, in which $R_4$ is $C_1$-$C_4$alkyl or $C_1$-$C_4$halogenalkyl and X represents a leaving group, such as halogen, mesylate or tosylate, in the presence of a base. The alkylation reaction is advantageously carried out in aprotic inert organic solvents. Such solvents are hydrocarbons such as benzene, toluene, xylene or cyclohexane, ethers such as diethyl ether, ethylene glycol dimethyl ether, diethylene glycol dimethyl ether, tetrahydrofuran or dioxane, amides such as N,N-dimethylformamide, diethylformamide or N-methylpyrrolidinone. The reaction temperatures are between –20° C. and +120° C. Suitable bases are inorganic bases such as hydrides, e.g. sodium hydride or calcium hydride, hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases. The bases can be used as such or else with catalytic amounts of a phase-transfer catalyst, for example crown ether, in particular 18-crown-6, or a tetraalkylammonium salt. The oximes of formula VIb can be obtained by reacting aldehyde or ketone IV with hydroxylamine hydrochloride from room temperature to reflux, preferably at room temperature, in an appropriate solvent such as methanol or ethanol in the presence of an appropriate alkali such as sodium hydroxide, potassium carbonate or pyridine. A general description of the synthesis of oximes with hydroxylamines is described in March, *Advanced Organic Chemistry*, 4$^{th}$ Ed, pp. 906-907 and references therein.

O-Alkylhydroxylamines of formula IIA may be prepared by the reduction of O-alkoxy oxime derivatives of formula VI. It will be appreciated by those skilled in the art that this reduction can be carried out with a number of different reducing agents.

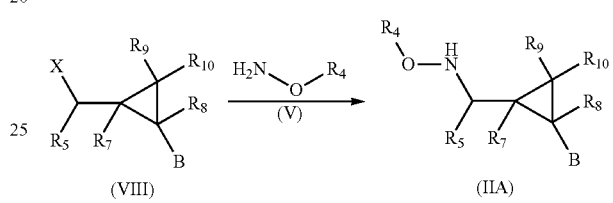

O-Alkylhydroxylamines of formula IIA may also prepared by the nucleophilic substitution of derivatives of formula VIII, in which $R_5$, $R_7$, $R_8$, $R_9$ and $R_{10}$ are as defined under formula I and X represents a leaving group, such as halogen, mesylate or tosylate, with a compound of formula V, in which $R_4$ is $C_1$-$C_4$alkyl or $C_1$-$C_4$halogenalkyl, in the presence of a base. The substitution reaction is advantageously carried out in aprotic inert organic solvents. The reaction temperatures are between 0° C. and +100° C. Suitable bases are, in particular pyridine, tertiary amines such as trimethylamine, triethylamine, huenig base, quinuclidine, 1,4-diazabicyclo[2.2.2]octane, 1,5-diazabicyclo[4.3.0]non-5-ene or 1,5-diazabicyclo[5.4.0]undec-7-ene. However, inorganic bases such as carbonates, sodium carbonate and potassium carbonate, or hydrogen carbonates such as potassium hydrogen carbonate and sodium hydrogen carbonate may also be used as bases.

The bases can be used as such or else with catalytic amounts of a phase-transfer catalyst, for example crown ether, in particular 18-crown-6, or a tetraalkylammonium salt.

Intermediates of the formula IV

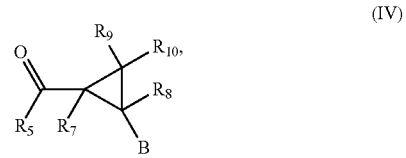

wherein $R_5$, $R_7$, $R_8$, $R_9$ and $R_{10}$ are as defined under formula I, may be prepared as described in reaction scheme below.

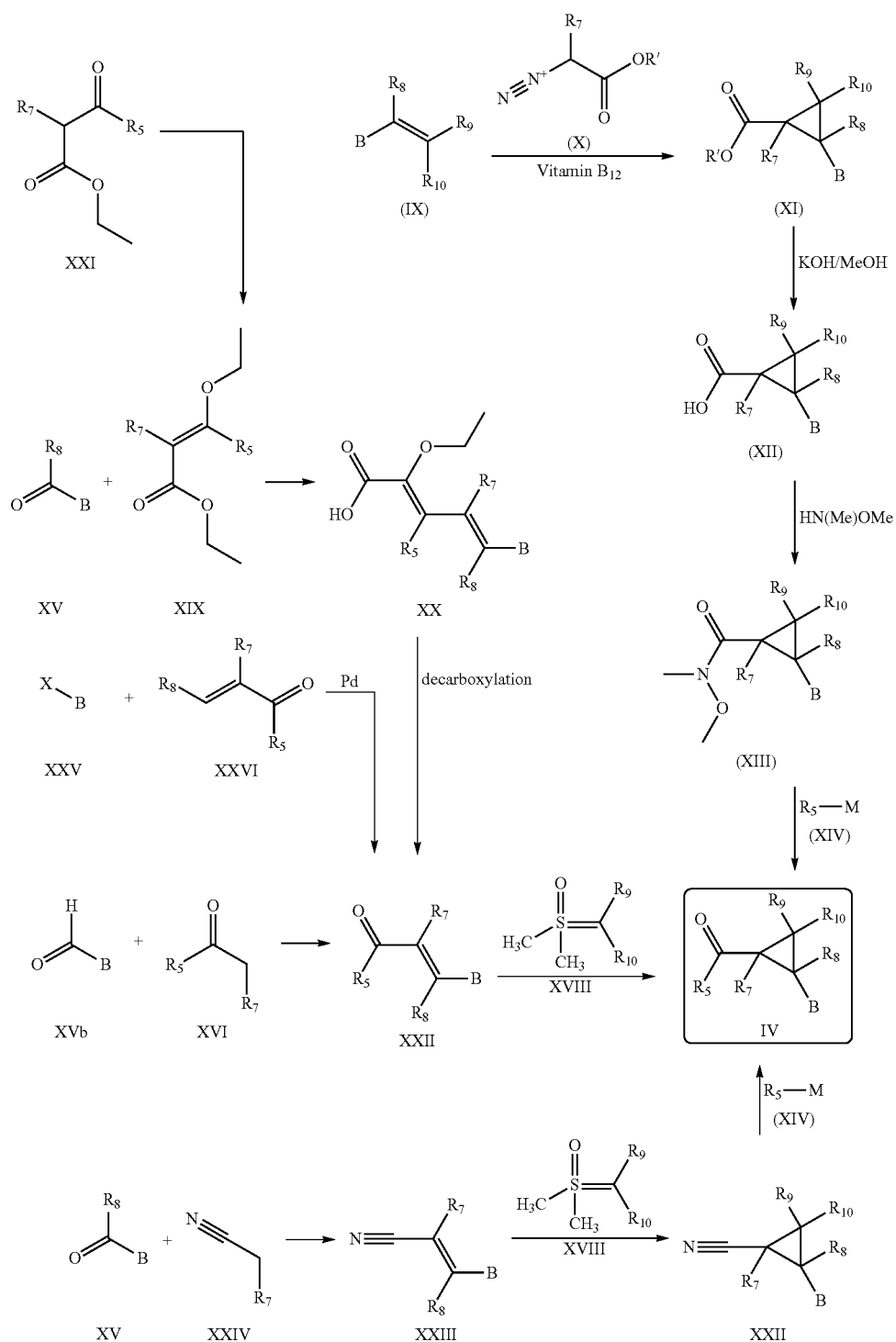

Reaction of compounds of formula IX, wherein $R_8$, $R_9$, $R_{10}$ and B are as defined under formula I, with alkyldiazoacetate derivatives of formula X, wherein $R_7$ is as defined under formula II and R' is $C_1$-$C_6$alkyl, and Vitamin $B_{12}$ as catalyst (Y. Chen and X. P. Zhang, J. Org. Chem. 2004, 69, 2431-2435), gives a diastereomeric mixture of cyclopropylcarboxylates of formula XI, wherein $R_7$, $R_8$, $R_9$, $R_{10}$ and B are as defined under formula II. The diastereomers can be separated either chromatographically or, after saponification, by recrystallisation of the corresponding carboxylic acids of formula XII, wherein $R_1$, $R_2$, $R_3$, $R_4$ and B are as defined under formula II. Said carboxylic acids can be converted to the corresponding Weinreb amide of formula XIII, wherein $R_7$, $R_8$, $R_9$, $R_{10}$ and B are as defined under formula II using N,O-dimethylhydroxylamine hydrochloride with a coupling reagent like EDC in the presence of a suitable base like N-methylmorpholine in an appropriate solvent such as dichloromethane. The Weinreb amide of formula XIII can be converted to the corresponding ketones of formula VI using Grignard reagents $R_5MgX$ or organolithium reagents $R_5Li$ addition of formula XIV, wherein $R_5$ is defined as under formula II in an inert solvent like THF at a suitable temperature.

The cyclopropanation is carried out at temperatures of between 0-100° C. in a convenient organic solvent such as methanol, ethanol, tert-butanol, trifluoroethanol, chloroform, dichloromethane or dioxane.

Other catalysts such as copper acetate can be used as an alternative to Vitamin $B_{12}$ for the cyclopropanation reaction.

The cyclopropyl aldehydes or ketones VI may also be prepared by conventional techniques. The unsaturated aldehyde or ketone XVII is reacted with a sulfur ylide of formula XVIII, prepared from a dimethylsulfoxonium salt in the presence of a base, resulting the substituted cyclopropanes VI. The chemistry of sulfur ylides was developed by Corey and Chaykovsky and is described in Trost and Melvin, *Sulfur Ylids*, Acd. Press, NY 1975 and in Block, *Reactions of Orqanosulfur Compounds*, pp. 91-123 Acd. Press, NY 1978. Typical reaction conditions for sulfur ylide formation from dimethylsulfoxonium salt utilizes bases such as hydroxides, metal hydrides and alkoxides in solvents such as dimethoxyethane, dimethylsulfoxide and water deepending on the base employed. The reaction conducted from 0-20° C. preferably from 10-15° C. and preferably with alkali metal hydroxides in dimethylsulfoxide. Typically dimethylsulfoxonium methylide is prepared from trimethylsulfoxonium iodide in dimethylsulfoxide in the presence of powdered sodium hydroxide at room temperature. The α,β-unsaturated aldehydes or ketones of formula XVII may prepared by conventional condensation techniques. A extensive description of the synthesis of α,β-unsaturated aldehydes or ketones (chalcones, enones) is described in March, *Advanced Organic Chemistry*, 4$^{th}$ Ed, pp. 937-955 and references therein. For example *Organic Reactions*, Volume 16 describes the general aldol condensation of ketones and aldehydes.

Aryl or heteroaryl aldehydes of formula XV where $R_8$ is hydrogen and B is defined under formula II are reacted with the ketones of formula XVI to provide the intermediates of formula XVII. Typically the ketone XVI is dissolved in a protic solvent such as methanol or ethanol, to which is added dropwise the aldehyde B, followed by the base. The reaction temperatures are between 0° C. and +35° C. Suitable bases are inorganic bases such as hydroxides, e.g. barium hydroxide, sodium hydroxide or potassium hydroxide.

When the enone XVII is derived from XVI=acetone ($R_5$ is methyl and $R_7$ is hydrogen) the solvent can be acetone. Preferably the aldehyde is dissolved in a mixture of acetone:water (1:5) to which is added the base while stirring at room temperature.

When $R_8$ is different from hydrogen and B is defined under formula II, compounds of formula XVII may be prepared according to the procedure described in U.S. Pat. No. 3,950,427, col. 17 line 20, to provide after purification the E diastereomere (B is trans to $R_8CO$).

In a typical preparation, ketone of formula XV is reacted with an ethyl trans 3-ethoxycrotonate of formula XIX in DMF in the presence of potassium t-butoxyde to form the intermediate of formula XX, to give after acidic hydrolysis and decarboxylation XVII.

The crotonates of formula XIX may be prepared from substituted acetoketones of formula XXI by conventional techniques. In another route XVII can be prepared by a Heck reaction of a halide XXV with an acryl ketone of formula XXVI.

Alternatively the cyclopropyl aldehydes or ketones of formula VI can be prepared from cyclopropyl nitriles of formula XXII which are prepared via cyclopropanation of the acrylonitriles of formula XXIII. The acrylonitriles of formula XXIII may be prepared by conventional synthetic methods as described in March, *Advanced Organic Chemistry*, 4$^{th}$ Ed, pp. 937-955 and references therein. For example the nitrile derivative of formula XXIV is condensed with the ketone or aldehyde of formula XVI in the presence of a base to provide the acrylonitrile XXIII. Typically a nitrile of formula XXIV is dissolved in a solvent such as ethanol and water to which is added the aldehyde or ketone of formula XV followed by a base. The reaction temperature is typically at ambient temperature. Suitable bases are alkali hydroxides such as barium hydroxide, sodium hydroxide or potassium hydroxide.

The acrylonitrile of formula XXIII is treated as described for XVIII with a sulphur ylide of formula XVIII to provide compounds of formula XXII.

The cyclopropyl nitrile of formula XXII is transformed to the cyclopropyl ketone VI by organometallic addition to the nitrile followed by hydrolysis. Standard Grignard reagents $R_5MgX$ or organolithium reagents $R_5Li$ add to the nitrile functionality to provide the ketone VI.

The addition reaction to nitriles is described in March, *Advanced Organic Chemistry*, 4$^{th}$ Ed, pp. 935-936 and references therein.

Cyclopropyl nitrile can be transformed to cyclopropyl aldehyde of formula VI where $R_5$ is hydrogen by standard reductive methods such as with Diisobutylaluminium hydride (DIBALH). The formation of aldehydes from the reduction of nitriles is described in March, *Advanced Organic Chemistry*, 4$^{th}$ Ed, pp. 919-920 and references therein.

Compounds of the formula IV, V, VII, VIII, IX, X, XI, XII, XIII, XIV, XV, XVI, XVII, XVIII, XIX, XX, XXI, XXII and XXIII are known and are commercially available or can be prepared according to the methods described in the above-mentioned references or according to methods generally known in the art.

Compounds of the formula III are known and partially commercially available. They can be prepared analogously as described, for example, in WO 00/09482, WO 02/38542, WO 2004/018438, EP-0-589-301, WO 93/11117 and Arch. Pharm. Res. 2000, 23(4), 315-323.

The compounds I and, where appropriate, the tautomers thereof, can, if appropriate, also be obtained in the form of hydrates and/or include other solvents, for example those which may have been used for the crystallization of compounds which are present in solid form.

It has now been found that the compounds of formula I according to the invention have, for practical purposes, a very advantageous spectrum of activities for protecting useful plants against diseases that are caused by phytopathogenic microorganisms, such as fungi, bacteria or viruses.

The invention therefore also relates to a method of controlling or preventing infestation of useful plants by phytopathogenic microorganisms, wherein a compound of formula I is applied as active ingredient to the plants, to parts thereof or the locus thereof. The compounds of formula I according to the invention are distinguished by excellent activity at low rates of application, by being well tolerated by plants and by being environmentally safe. They have very useful curative, preventive and systemic properties and are used for protecting numerous useful plants. The compounds of formula I can be used to inhibit or destroy the diseases that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds of formula I according to the invention may be used for controlling fungi in related areas, for example in the protection of technical materials, including wood and wood related technical products, in food storage or in hygiene management.

The compounds of formula I are, for example, effective against the phytopathogenic fungi of the following classes: Fungi imperfecti (e.g. *Botrytis, Pyricularia, Helminthosporium, Fusarium, Septoria, Cercospora* and *Alternaria*) and Basidiomycetes (e.g. *Rhizoctonia, Hemileia, Puccinia*). Additionally, they are also effective against the Ascomycetes classes (e.g. *Venturia* and *Erysiphe, Podosphaera, Monilinia, Uncinula*) and of the Oomycetes classes (e.g. *Phytophthora, Pythium, Plasmopara*). Outstanding activity has been observed against powdery mildew (*Erysiphe* spp.). Furthermore, the novel compounds of formula I are effective against phytopathogenic bacteria and viruses (e.g. against *Xanthomonas spp, Pseudomonas spp, Erwinia amylovora* as well as against the tobacco mosaic virus). Good activity has been observed against Asian soybean rust (*Phakopsora pachyrhizi*).

Within the scope of the invention, useful plants to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamomum, camphor) or plants such as tobacco, nuts, coffee, eggplants, sugar cane, tea, pepper, vines, hops, bananas and natural rubber plants, as well as ornamentals.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

Examples of such plants are: YieldGard® (maize variety that expresses a CryIA(b) toxin); YieldGard Rootworm® (maize variety that expresses a CryIIIB($B_1$) toxin); YieldGard Plus® (maize variety that expresses a CryIA(b) and a CryIIIB ($B_1$) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® Agrisure® GT Advantage (GA21 glyphosate-tolerant trait), Agrisure® CB Advantage (Bt11 corn borer (CB) trait), Agrisure® RW (corn rootworm trait) and Protecta®.

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compounds of formula I can be used in unmodified form or, preferably, together with carriers and adjuvants conventionally employed in the art of formulation.

Therefore the invention also relates to compositions for controlling and protecting against phytopathogenic microorganisms, comprising a compound of formula I and an inert carrier, and to a method of controlling or preventing infestation of useful plants by phytopathogenic microorganisms, wherein a composition, comprising a compound of formula I as active ingredient and an inert carrier, is applied to the plants, to parts thereof or the locus thereof.

To this end compounds of formula I and inert carriers are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula I or compositions, comprising a compound of formula I as active ingredient and an inert carrier, can be applied to the locus of the plant or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

A preferred method of applying a compound of formula I, or a composition, comprising a compound of formula I as active ingredient and an inert carrier, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation, i.e. a composition comprising the compound of formula I and, if desired, a solid or liquid adjuvant, is prepared in a known manner, typically by intimately mixing and/or grinding the compound with extenders, for example solvents, solid carriers and, optionally, surface-active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds. The rate of application for the desired action can be determined by experiments. It depends for example on the type of action, the developmental stage of the useful plant, and on the application (location, timing, application method) and can, owing to these parameters, vary within wide limits.

The compounds of formula (I), or a pharmaceutical salt thereof, described above may also have an advantageous spectrum of activity for the treatment and/or prevention of microbial infection in an animal. "Animal" can be any animal, for example, insect, mammal, reptile, fish, amphibian, preferably mammal, most preferably human. "Treatment" means the use on an animal which has microbial infection in order to reduce or slow or stop the increase or spread of the infection, or to reduce the infection or to cure the infection. "Prevention" means the use on an animal which has no apparent signs of microbial infection in order to prevent any future infection, or to reduce or slow the increase or spread of any future infection.

According to the present invention there is provided the use of a compound of formula (I) in the manufacture of a medicament for use in the treatment and/or prevention of microbial infection in an animal. There is also provided the use of a compound of formula (I) as a pharmaceutical agent. There is also provided the use of a compound of formula (I) as an antimicrobial agent in the treatment of an animal. According to the present invention there is also provided a pharmaceutical composition comprising as an active ingredient a compound of formula (I), or a pharmaceutically acceptable salt thereof, and a pharmaceutically acceptable diluent or carrier. This composition can be used for the treatment and/or prevention of antimicrobial infection in an animal. This pharmaceutical composition can be in a form suitable for oral administration, such as tablet, lozenges, hard capsules, aqueous suspensions, oily suspensions, emulsions dispersible powders, dispersible granules, syrups and elixirs. Alternatively this pharmaceutical composition can be in a form suitable for topical application, such as a spray, a cream or lotion. Alternatively this pharmaceutical composition can be in a form suitable for parenteral administration, for example injection. Alternatively this pharmaceutical composition can be in inhalable form, such as an aerosol spray.

The compounds of formula (I) may be effective against various microbial species able to cause a microbial infection in an animal. Examples of such microbial species are those causing Aspergillosis such as *Aspergillus fumigatus, A. flavus, A. terrus, A. nidulans* and *A. niger*; those causing Blastomycosis such as *Blastomyces dermatitidis*; those causing Candidiasis such as *Candida albicans, C. glabrata, C. tropicalis, C. parapsilosis, C. krusei* and *C. lusitaniae*; those causing Coccidioidomycosis such as *Coccidioides immitis*; those causing Cryptococcosis such as *Cryptococcus neoformans*; those causing Histoplasmosis such as *Histoplasma capsulatum* and those causing Zygomycosis such as *Absidia corymbifera, Rhizomucor pusillus* and *Rhizopus arrhizus*. Further examples are *Fusarium* Spp such as *Fusarium oxysporum* and *Fusarium solani* and *Scedosporium* Spp such as *Scedosporium apiospermum* and *Scedosporium prolificans*. Still further examples are *Microsporum* Spp, *Trichophyton* Spp, *Epidermophyton* Spp, *Mucor* Spp, *Sporothorix* Spp, *Phialophora* Spp, *Cladosporium* Spp, *Petriellidium* spp, *Paracoccidioides* Spp and *Histoplasma* Spp.

The following non-limiting Examples illustrate the above-described invention in greater detail without limiting it.

PREPARATORY EXAMPLES

Example P1

Preparation of trans 3-difluoromethyl-1-methyl-1H-pyrazole-4-carboxylic acid {1-[2-(2-chloro-phenyl)-cyclopropyl]-ethyl}-methoxy-amide (compound 1.011 diastereomere A)

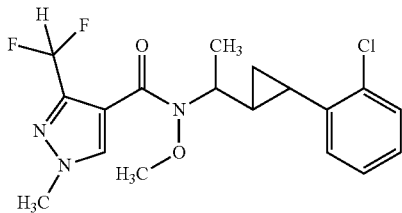 [SMILES: CON(C(=O)c1cn(C)nc1C(F)F)C(C)C1CC1c1ccccc1Cl]

To a stirred solution of trans N-{1-[2-(2-chloro-phenyl)-cyclopropyl]-ethyl}-O-methyl-hydroxylamine diastereomere A (0.42 g; 1.9 mmol) prepared as described in example P12 and triethylamine (0.34 mL; 2.5 mmol) in dichloromethane (7.0 ml) at ambient temperature was added dropwise 3-difluoromethyl-1-methyl-1H-pyrazole-4-carbonyl chloride (0.38 g; 1.9 mmol).

The reaction mixture was stirred for 16 hours at ambient temperature then poured in water (50 mL) and extracted with dichloromethane (3×25 ml). Combined organic layers were washed with water (10 mL), brine and dried over anhydrous sodium sulphate. The solvent was removed in vacuo and the residue was purified by flash chromatography over silica gel (elution gradient: cyclohexane/ethyl acetate 99:1 to 1:99) to afford 0.70 g (100% of theory) of trans 3-difluoromethyl-1-methyl-1H-pyrazole-4-carboxylic acid {1-[2-(2-chloro-phenyl)-cyclopropyl]-ethyl}-methoxy-amide as single diastereomere A in form of a clear viscous oil.

$^1$H NMR (400 MHz, CDCl$_3$): 0.98-1.03 (m, 1H); 1.12-1.17 (m, 1H); 1.45-1.52 (m, 1H); 1.51 (d, 3H); 2.23-2.28 (m, 1H); 3.77 (s, 3H); 3.99 (s, 3H); 4.07-4.16 (m, 1H); 6.93-6.95 (m, 1H); 7.10-7.20 (m, 2H); 7.10+7.24+7.38 (t, 1H); 7.35-7.37 (m, 1H); 7.91 (s, 1H).

MS [M+H]$^+$: 384/386.

Example P2

Preparation of trans 3-difluoromethyl-1-methyl-1H-pyrazole-4-carboxylic acid {1-[2-(2-chloro-phenyl)-cyclopropyl]-ethyl}-methoxy-amide (compound 1.011 diastereomere B)

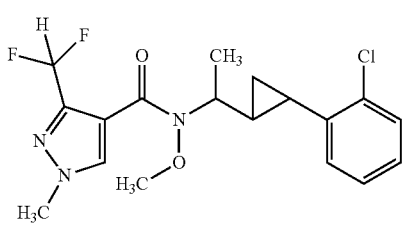 [SMILES: CON(C(=O)c1cn(C)nc1C(F)F)C(C)C1CC1c1ccccc1Cl]

To a stirred solution of trans N-{1-[2-(2-chloro-phenyl)-cyclopropyl]-ethyl}-O-methyl-hydroxylamine (0.30 g; 1.3 mmol) prepared as described in example P12 and triethylamine (0.25 ml; 1.7 mmol) in dichloromethane (5.0 ml) at ambient temperature was added dropwise 3-difluoromethyl-1-methyl-1H-pyrazole-4-carbonyl chloride (0.28 g; 1.3 mmol). The reaction mixture was stirred for 16 hours at ambient temperature then poured in water (50 ml) and extracted with dichloromethane (3×25 ml). Combined organic layers were washed with water (10 ml), brine and dried over anhydrous sodium sulphate. The solvent was removed in vacuo and the residue was purified by flash chromatography over silica gel (elution gradient: cyclohexane/ethyl acetate 99:1 to 1:99) to afford 0.46 g (92% of theory) of trans 3-Difluoromethyl-1-methyl-1H-pyrazole-4-carboxylic acid {1-[2-(2-chloro-phenyl)-cyclopropyl]-ethyl}-methoxy-amide as single diastereomere A in form of a clear viscous oil.

$^1$H NMR (400 MHz, CDCl$_3$): 1.02-1.07 (m, 1H); 1.10-1.15 (m, 1H); 1.44 (d, 3H); 1.48-1.55 (m, 1H); 2.36-2.42 (m, 1H); 3.65 (s, 3H); 3.96 (s, 3H); 4.09-4.17 (m, 1H); 6.88-6.90 (m, 1H); 7.06-7.17 (m, 2H); 7.09+7.23+7.37 (t, 1H); 7.27-7.31 (m, 1H); 7.86 (s, 1H).

MS [M+H]$^+$: 384/386.

Example P3

Preparation of trans-3-difluoromethyl-1-methyl-1H-pyrazole-4-carboxylic acid {1-[2-(2,4-dichlorophenyl)-cyclopropyl]-ethyl}-methoxy-amide (compound 1.018 diastereomere A)

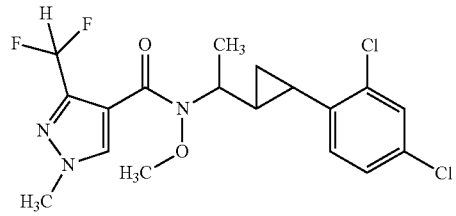

A solution of 3-difluoromethyl-1-methyl-1H-pyrazole-4-carbonyl chloride (80 mg; 0.41 mmol) in acetonitrile (1 ml) was added dropwise to a stirred mixture of trans-N-{1-[2-(2,4-dichlorophenyl)-cyclopropyl]-ethyl}-O-methyl-hydroxylamine diastereomere A (88 mg; 0.34 mmol), prepared as described in example P13 and DABCO (54 mg; 0.48 mmol) in acetonitrile (1 ml) at ambient temperature. The reaction mixture was stirred for 16 hours at ambient temperature. The solvent was removed in vacuo and the residue was purified by flash chromatography over silica gel (10 g) (eluent: n-hexane/ethyl acetate 1:1).

0.12 g (84.0% of theory) of 3-difluoromethyl-1-methyl-1H-pyrazole-4-carboxylic acid {1-[2-(2,4-dichlorophenyl)-cyclopropyl]-ethyl}-methoxy-amide was obtained as single diastereomere A in form of a solid. Mp 133-135° C.

$^1$H NMR (400 MHz, CDCl$_3$): 0.82-1.02 (m, 2H); 1.12-1.59 (m, 1H); 1.49-1.53 (d, 3H); 2.15-2.23 (m, 1H); 3.78 (1s, 3H); 4.00 (s; 3H); 4.04-4.14 (m, 1H); 6.85-6.89 (d, 1H); 7.04-7.43 (t, 1H, CHF$_2$); 7.13-7.18 (dd, 1H); 7.37-7.39 (d, 1H); 7.91 (s, 1H).

MS [M+H]$^+$: 418/420/422.

Example P4

Preparation of trans-3-difluoromethyl-1-methyl-1H-pyrazole-4-carboxylic acid {1-[2-(2,4-dichlorophenyl)-cyclopropyl]-ethyl}-methoxy-amide (compound 1.018 diastereomere B)

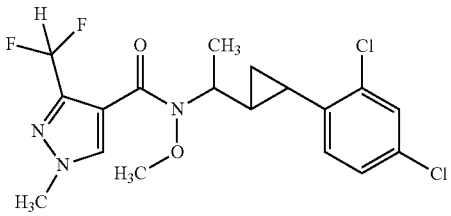 [SMILES: CON(C(=O)c1cn(C)nc1C(F)F)C(C)C1CC1c1ccc(Cl)cc1Cl]

A solution of 3-difluoromethyl-1-methyl-1H-pyrazole-4-carbonyl chloride (80 mg; 0.41 mmol) in acetonitrile (1 ml) was added dropwise to a stirred mixture of trans-N-{1-[2-(2,4-dichlorophenyl)-cyclopropyl]-ethyl}-O-methyl-hydroxylamine diastereomere B (88 mg; 0.34 mmol), prepared as described in example P13 and DABCO (54 mg; 0.48 mmol) in acetonitrile (1 ml) at ambient temperature. The reaction mixture was stirred for 16 hours at ambient temperature. The solvent was removed in vacuo and the residue was purified by flash chromatography over silica gel (10 g) (eluent: n-hexane/ethyl acetate 1:1).

90 mg (63.0% of theory) of 3-difluoromethyl-1-methyl-1H-pyrazole-4-carboxylic acid {1-[2-(2,4-dichlorophenyl)-cyclopropyl]-ethyl}-methoxy-amide was obtained as single diastereomere B in form of a solid. Mp 142-144° C.

$^1$H NMR (400 MHz, CDCl$_3$): 1.02-1.14 (m, 2H); 1.43-1.48 (d, 3H); 1.43-1.58 (m, 1H); 2.28-2.37 (m, 1H); 3.65 (1s, 3H); 3.96 (s; 3H); 4.05-4.17 (m, 1H); 6.79-6.83 (d, 1H); 7.04-7.43 (t, 1H, CHF2); 7.12-7.16 (dd, 1H); 7.31-7.33 (d, 1H); 7.95 (s, 1H).

MS [M+H]$^+$: 418/420/422.

Example P5

Preparation of trans 3-difluoromethyl-1-methyl-1H-pyrazole-4-carboxylic acid{1-[2-(2-chloro-6-fluoro-phenyl)-cyclopropyl]-ethyl}-methoxy-amide (compound 1.027)

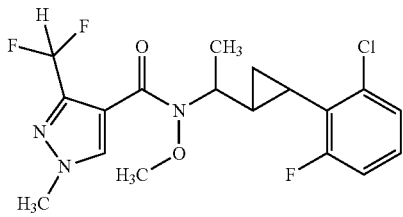

To a stirred solution of trans N-{1-[2-(2-Chloro-6-fluoro-phenyl)-cyclopropyl]-ethyl}-O-methyl-hydroxylamine (0.80 g; 3.3 mmol) prepared as described in example P14 and triethylamine (0.60 ml; 4.3 mmol) in dichloromethane (10 ml) at ambient temperature was added dropwise 3-difluoromethyl-1-methyl-1H-pyrazole-4-carbonyl chloride (0.64 g; 3.3 mmol). The reaction mixture was stirred for 16 hours at ambient temperature then poured in water (60 ml) and extracted with dichloromethane (3×25 ml). Combined organic layers were washed with water (10 ml), brine and dried over anhydrous sodium sulphate. The solvent was removed in vacuo and the residue was purified by flash chromatography over silica gel (elution gradient: cyclohexane/ethyl acetate 99:1 to 1:99) to afford 1.30 g (100% of theory) of trans 3-difluoromethyl-1-methyl-1H-pyrazole-4-carboxylic acid {1-[2-(2-chloro-6-fluoro-phenyl)-cyclopropyl]-ethyl}-methoxy-amide as a clear viscous oil.

$^1$H NMR (400 MHz, CDCl$_3$): 0.99-1.32 (4m, 2H); 1.44+1.54 (2d, 3H); 1.75-2.14 (3m, 2H); 3.71+3.78 (2s; 3H); 3.98+3.99 (2s, 3H); 4.04-4.23 (2m, 1H); 6.83-6.94 (m, 1H); 7.02-7.17 (m, 2H); 7.10+7.24+7.38 (t, 1H); 7.91+7.92 (2s, 1H).

MS [M+H]$^+$: 402/404.

Example P6

Preparation of trans-3-difluoromethyl-1-methyl-1H-pyrazole-4-carboxylic acid {1-[2-(2,6-dichlorophenyl)-cyclopropyl]-ethyl}-methoxy-amide (compound 1.028)

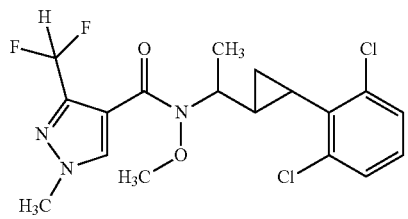 [SMILES: CON(C(=O)c1cn(C)nc1C(F)F)C(C)C1CC1c1c(Cl)cccc1Cl]

A solution of 3-difluoromethyl-1-methyl-1H-pyrazole-4-carbonyl chloride (243 mg; 1.25 mmol) in acetonitrile (1 ml) was added dropwise to a stirred mixture of trans-N-{1-[2-(2,6-dichlorophenyl)-cyclopropyl]-ethyl}-O-methyl-hydroxylamine (270 mg; 1.04 mmol), prepared as described in example P15 and DABCO (175 mg; 1.56 mmol) in acetonitrile (1 ml) at ambient temperature. The reaction mixture was stirred for 16 hours at ambient temperature. The solvent was removed in vacuo and the residue was purified by flash chromatography over silica gel (10 g) (eluent: n-hexane/ethyl acetate 1:2).

0.33 g (76.0% of theory) of trans-3-difluoromethyl-1-methyl-1H-pyrazole-4-carboxylic acid {1-[2-(2,6-dichlorophenyl)-cyclopropyl]-ethyl}-methoxy-amide was obtained as a mixture of diastereomers in form of a high viscous oil.

$^1$H NMR (400 MHz, CDCl$_3$): 0.81-1.68 (m, 6H); 1.78-2.02 (m, 1H); 3.75+3.78 (2s, 3H); 3.96+3.97 (2s; 3H); 4.04-4.18 (m, 1H); 7.03-7.18 (m, 1H); 7.22-7.29 (m, 2H); 7.89+7.93 (2s, 1H).

MS [M+H]$^+$: 418/420/422.

Example P7

Preparation of trans-3-difluoromethyl-1-methyl-1H-pyrazole-4-carboxylic acid {1-[2-(2,4,6-trichlorophenyl)-cyclopropyl]-ethyl}-methoxy-amide (compound 1.034)

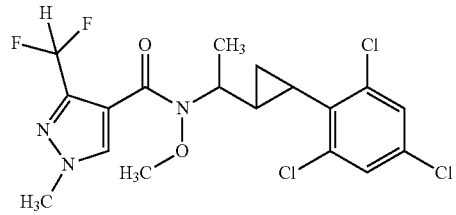 [SMILES: CON(C(=O)c1cn(C)nc1C(F)F)C(C)C1CC1c1c(Cl)cc(Cl)cc1Cl]

A solution of 3-difluoromethyl-1-methyl-1H-pyrazole-4-carbonyl chloride (24 mg; 0.12 mmol) in acetonitrile (1 ml) was added dropwise to a stirred mixture of N-{1-[2-(2,4,6-trichlorophenyl)-cyclopropyl]-ethyl}-O-methyl-hydroxylamine (24 mg; 0.08 mmol), prepared as described in example P16 and DABCO (14 mg; 0.12 mmol) in acetonitrile (1 ml) at ambient temperature. The reaction mixture was stirred for 2 hours at ambient temperature. The solvent was removed in vacuo and the residue was purified by flash chromatography over silica gel (4 g) (eluent: n-hexane/ethyl acetate 1:2).

30 mg (83.0% of theory) of 3-difluoromethyl-1-methyl-1H-pyrazole-4-carboxylic acid {1-[2-(2,4,6-trichlorophenyl)-cyclopropyl]-ethyl}-methoxy-amide was obtained as a mixture of diastereomers in form of a high viscous oil.

$^1$H NMR (400 MHz, CDCl$_3$): 0.80-1.70 (m, 6H); 1.72-1.95 (m, 1H); 3.75+3.78 (2s, 3H); 3.96+3.97 (2s; 3H); 4.04-4.18+ 4.46-4.55 (m, 1H); 7.03-7.42+7.06-7.48 (2t, 1H, CHF2); 7.24+7.26 (2s, 2H); 7.89+7.93 (2s, 1H).

MS [M+H]$^+$: 452/454/456.

Example P8

Preparation of trans 3-Difluoromethyl-1-methyl-1H-pyrazole-4-carboxylic acid methoxy-{1-[2-(2,4,5-trichloro-thiophen-3-yl)-cyclopropyl]-ethyl}-amide (compound 1.063)

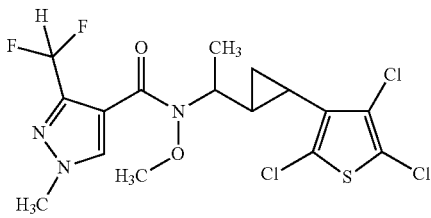 [SMILES: CON(C(=O)c1cn(C)nc1C(F)F)C(C)C1CC1c1c(Cl)sc(Cl)c1Cl]

To a stirred solution of trans O-Methyl-N-{1-[2-(2,4,5-trichloro-thiophen-3-yl)-cyclopropyl]ethyl}-hydroxylamine (0.25 g; 0.83 mmol) prepared as described in example P17 and triethylamine (0.15 mL; 1.08 mmol) in dichloromethane (5.0 ml) at ambient temperature was added dropwise 3-difluoromethyl-1-methyl-1H-pyrazole-4-carbonyl chloride (0.16 g; 0.83 mmol). The reaction mixture was stirred for 16 hours at ambient temperature then poured in water (3 ml) and extracted with dichloromethane (3×1 ml). Combined organic layers were washed with water (1 ml), brine and dried over anhydrous sodium sulphate. The solvent was removed in vacuo and the residue was purified by flash chromatography over silica gel (elution gradient: cyclohexane/ethyl acetate 99:1 to 30:70) to afford 0.32 g (84% of theory) of trans 3-difluoromethyl-1-methyl-1H-pyrazole-4-carboxylic acid methoxy-{1-[2-(2,4,5-trichloro-thiophen-3-yl)-cyclopropyl]-ethyl}-amide as white solid (m.p. 110° C.-113° C.).

$^1$H NMR (400 MHz, CDCl$_3$): 0.94-1.35 (4m, 2H); 1.44+1.57 (2d, 3H); 1.68-1.95 (4m, 2H); 3.73+3.78 (2s; 3H); 3.99 (s, 3H); 3.99-4.21 (2m, 1H); 7.09-7.38 (2t, 1H); 7.87+7.91 (2s, 1H).

MS [M+MeCN+Na]$^+$: 521/523/525.

MS [M+Na]$^+$: 480/482/484.

Example P9

Preparation of trans 3-difluoromethyl-1-methyl-1H-pyrazole-4-carboxylic acid {1-[2-(5-chloro-thiophen-2-yl)-cyclopropyl]-ethyl}-methoxy-amide (compound 1.070)

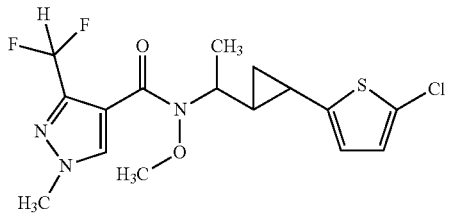 [SMILES: CON(C(=O)c1cn(C)nc1C(F)F)C(C)C1CC1c1ccc(Cl)s1]

To a stirred solution of trans N-{1-[2-(5-Chloro-thiophen-2-yl)-cyclopropyl]-ethyl}-O-methyl-hydroxylamine (0.19 g; 0.83 mmol) prepared as described in example P18 and triethylamine (0.16 ml; 1.08 mmol) in dichloromethane (5.0 ml) at ambient temperature was added dropwise 3-difluoromethyl-1-methyl-1H-pyrazole-4-carbonyl chloride (0.16 g; 0.83 mmol). The reaction mixture was stirred for 16 hours at ambient temperature then poured in water (3 ml) and extracted with dichloromethane (3×1 ml). Combined organic layers were washed with water (1 ml) and dried over anhydrous sodium sulphate. The solvent was removed in vacuo and the residue was purified by flash chromatography over silica gel (elution gradient: cyclohexane/ethyl acetate 99:1 to 30:70) to afford 0.31 g (97% of theory) of trans 3-difluoromethyl-1-methyl-1H-pyrazole-4-carboxylic acid {1-[2-(5-chloro-thiophen-2-yl)-cyclopropyl]-ethyl}-methoxy-amide as a resin.

$^1$H NMR (400 MHz, CDCl$_3$): 0.92-1.15 (4m, 2H); 1.40+1.44 (2d, 3H); 1.43-1.52 (m, 1H); 1.95-2.15 (2m, 1H); 3.71+3.77 (2s, 3H); 3.99 (s, 3H); 3.95-4.07 (m, 1H); 6.48+6.53 (2d, 1H); 6.64+6.69 (2d, 1H); 7.08+7.22+7.36 (2t, 1H); 7.90 (s, 1H).

MS [M+H]$^+$: 390/392.

Example P10

Preparation of trans 1-methyl-3-trifluoromethyl-1H-pyrazole-4-carboxylic acid methoxy-{1-[2-(2,4,5-trichloro-thiophen-3-yl)-cyclopropyl]-ethyl}-amide (compound 2.063)

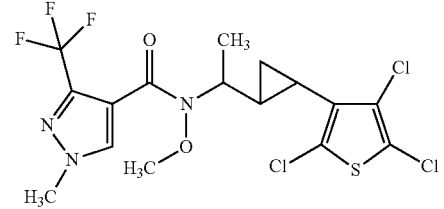 [SMILES: CON(C(=O)c1cn(C)nc1C(F)(F)F)C(C)C1CC1c1c(Cl)sc(Cl)c1Cl]

To a stirred solution of trans O-methyl-N-{1-[2-(2,4,5-trichloro-thiophen-3-yl)-cyclopropyl]ethyl}-hydroxylamine (0.25 g; 0.83 mmol) prepared as described in example P17 and triethylamine (0.16 ml; 1.08 mmol) in dichloromethane (5.0 ml) at ambient temperature was added dropwise 1-methyl-3-trifluoromethyl-1H-pyrazole-4-carbonyl chloride (0.18 g; 0.83 mmol). The reaction mixture was stirred for 16 hours at ambient temperature then poured in water (3 ml) and extracted with dichloromethane (3×1 ml). Combined organic layers were washed with water (1 ml), brine and dried over anhydrous sodium sulphate. The solvent was removed in vacuo and the residue was purified by flash chromatography over silica gel (elution gradient: cyclohexane/ethyl acetate 99:1 to 30:70) to afford 0.34 g (85% of theory) of trans 1-methyl-3-trifluoromethyl-1H-pyrazole-4-carboxylic acid methoxy-{1-[2-(2,4,5-trichloro-thiophen-3-yl)-cyclopropyl]-ethyl}-amide as a resin.

$^1$H NMR (400 MHz, CDCl$_3$): 0.94-1.38 (4m, 2H); 1.42+1.57 (2d, 3H); 1.66-1.98 (3m, 2H); 3.63+3.67 (2s, 3H); 3.99 (s, 3H); 4.09-4.15 (m, 1H); 7.82+7.83 (2s, 1H).

MS [M+H]$^+$476/478/480.

Example P11

Preparation of trans 1-methyl-3-trifluoromethyl-1H-pyrazole-4-carboxylic acid {1-[2-(5-chloro-thiophen-2-yl)-cyclopropyl]-ethyl}-methoxy-amide (compound 2.070)

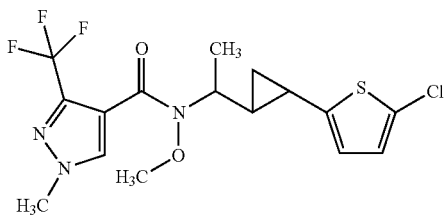 [SMILES: CON(C(=O)c1cn(C)nc1C(F)(F)F)C(C)C1CC1c1ccc(Cl)s1]

To a stirred solution of trans N-{1-[2-(5-chloro-thiophen-2-yl)-cyclopropyl]-ethyl}-O-methyl-hydroxylamine (0.19 g; 0.83 mmol) prepared as described in example P18 and triethylamine (0.16 ml; 1.08 mmol) in dichloromethane (5.0 ml) at ambient temperature was added dropwise 1-methyl-3-trifluoromethyl-1H-pyrazole-4-carbonyl chloride (0.18 g; 0.83 mmol). The reaction mixture was stirred for 16 hours at ambient temperature then poured in water (3 ml) and extracted with dichloromethane (3×1 ml). Combined organic layers were washed with water (1 ml) and dried over anhydrous sodium sulphate. The solvent was removed in vacuo and the residue was purified by flash chromatography over silica gel (elution gradient: cyclohexane/ethyl acetate 99:1 to 30:70) to afford 0.26 g (79% of theory) of 1-methyl-3-trifluoromethyl-1H-pyrazole-4-carboxylic acid {1-[2-(5-chloro-thiophen-2-yl)-cyclopropyl]-ethyl}-methoxy-amide as a resin.

$^1$H NMR (CDCl$_3$, 400 MHz): 0.92-1.15 (4m, 2H); 1.40+1.44 (2d, 3H); 1.45-1.52 (m, 1H); 1.94-2.17 (2m, 1H); 3.60+3.66 (2s, 3H); 3.98 (s, 3H); 3.91-4.03 (m, 1H); 6.49+6.53 (2d, 1H); 6.66+6.69 (2d, 1H); 7.82 (s, 1H).

MS [M+H]$^+$408/410.

Example P12

Preparation of trans N-{1-[2-(2-chloro-phenyl)-cyclopropyl]-ethyl}-O-methyl-hydroxylamine (diastereomeres A&B)

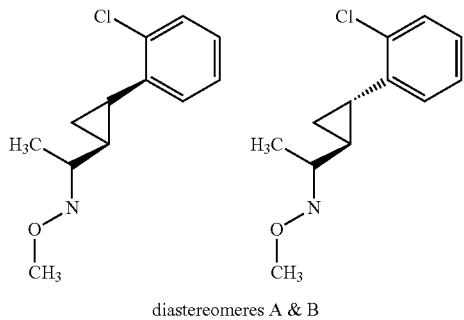

diastereomeres A & B

To a stirred solution of trans 1-[2-(2-chloro-phenyl)-cyclopropyl]-ethanone O-methyl-oxime (1.1 g; 5 mmol) prepared as described in example P19 in acetic acid (10 ml) at ambient temperature was added portionwise sodium cyanoborohydride (0.65 g; 10 mmol). The reaction mixture was stirred for 16 hours at ambient temperature then poured on saturated sodium hydrogen carbonate solution (50 ml) and extracted with dichloromethane (3×50 ml). Combined organic layers were dried over anhydrous sodium sulphate. The solvent was removed in vacuo and the residue was purified by flash chromatography over silica gel (elution gradient: cyclohexane/ethyl acetate 99:1 to 1:99) to afford 0.33 g (30% of theory) trans N-{1-[2-(2-Chloro-phenyl)-cyclopropyl]-ethyl}-O-methyl-hydroxylamine diastereomer A as a clear viscous oil and 0.46 g (41% of theory) and trans N-{1-[2-(2-Chloro-phenyl)-cyclopropyl]-ethyl}-O-methyl-hydroxylamine diastereomer B as a clear viscous oil.

Diastereomere A:

$^1$H NMR (CDCl$_3$, 400 MHz): 0.86-0.99 (2m, 2H); 1.04-1.11 (m, 1H) 1.22 (d, 3H); 2.14-2.18 (m, 1H); 2.52-2.59 (m, 1H); 3.54 (s; 3H); 5.7-6.2 (b, 1H); 6.89-6.91 (dd, 1H); 7.06-7.16 (m, 2H); 7.32-7.34 (dd, 1H).

MS [M+H]$^+$: 226/228.

Diastereomere B:

$^1$H NMR (CDCl$_3$, 400 MHz): 0.96-1.05 (m, 1H); 1.08-1.15 (m, 1H); 1.27 (d, 3H); 2.07-2.11 (m, 1H); 2.52-2.58 (m, 1H); 3.59 (s; 3H); 4.5-5.5 (b, 1H); 6.89-6.92 (dd, 1H); 7.08-7.17 (m, 2H); 7.33-7.35 (dd, 1H).

MS [M+H]$^+$226/228.

Example P13

Preparation of trans-N-{1-[2-(2,4-dichlorophenyl)-cyclopropyl]-ethyl}-O-methyl-hydroxylamine (diastereomeres A&B)

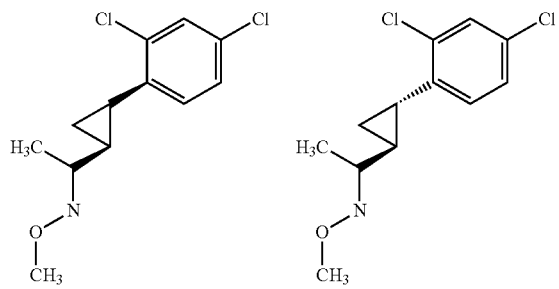

diastereomeres A & B

A solution of 1-[2-(2,4-dichloro-phenyl)-cyclopropyl]-ethanone O-methyl-oxime (188 mg, 0.73 mmol), prepared as described in example P20, in ethanol (2 ml) and acetic acid (1 ml) was treated at ambient temperature with sodium cyanoborohydride (136 mg, 2.19 mmol) added in one portion. The resulting solution was stirred at 24° C. for 10 hours. The solvent was evaporated under reduced pressure (co-evaporation with toluene twice) and the residue was slurried with 1 M NaOH (15 ml). The aqueous phase was extracted with ether (3×10 ml), washed with brine and dried over anhydrous Na$_2$SO$_4$. After removal of the solvent, the residue was purified by flash chromatography over silica gel (15 g) (eluent: c-hexane/ethyl acetate 3:1). 88 mg (45.0% of theory) of trans-N-{1-[2-(2,4-dichlorophenyl)-cyclopropyl]-ethyl}-O-methyl-hydroxylamine diastereomere A was obtained in form of a clear liquid.

¹H NMR: (CDCl₃, 400 MHz): 0.86-1.13 (m, 3H); 1.24-1.27 (d, 3H); 1.98-2.07 (m, 1H); 2.50-2.61 (m, 1H); 3.58 (s, 3H); 5.65 (s_br,1H); 6.82-6.86 (d, 1H); 7.12-7.16 (dd, 1H); 7.37-7.38 (dd, 1H).

MS [M+H]⁺: 260/262/264.

88 mg (45.0% of theory) of trans-N-{1-[2-(2,4-dichlorophenyl)-cyclopropyl]-ethyl}-O-methyl-hydroxylamine diastereomere B was obtained in form of a clear liquid.

¹H NMR: (CDCl₃, 400 MHz): 0.85-0.94 (m, 2H); 1.02-1.12 (m, 1H); 1.21-1.23 (d, 3H); 2.08-2.16 (m, 1H); 2.50-2.59 (m, 1H); 3.53 (s, 3H); 5.82 (s_br,1H); 6.82-6.86 (d, 1H); 7.11-7.15 (dd, 1H); 7.36-7.37 (dd, 1H).

MS [M+H]⁺: 260/262/264.

Example P14

Preparation of trans N-{1-[2-(2-chloro-6-fluoro-phenyl)-cyclopropyl]-ethyl}-O-methyl-hydroxylamine

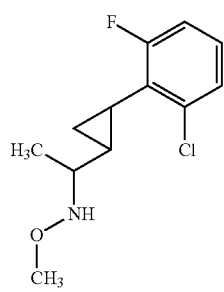

To a stirred solution of trans 1-[2-(2-chloro-6-fluoro-phenyl)-cyclopropyl]-ethanone O-methyl-oxime (1.1 g; 4.6 mmol) prepared as described in example P21, in acetic acid (10 ml) at ambient temperature was added portionwise sodium cyanoborohydride (0.60 g; 9.3 mmol). The reaction mixture was stirred for 16 hours at ambient temperature then poured in sodium hydrogen carbonate saturated solution (50 ml) and extracted with dichloromethane (3×50 ml). Combined organic layers were dried over anhydrous sodium sulphate. The solvent was removed in vacuo and the residue was purified by flash chromatography over silica gel (elution gradient: cyclohexane/ethyl acetate 99:1 to 1:99) to afford 0.85 g (75% of theory) of trans N-{1-[2-(2-chloro-6-fluoro-phenyl)-cyclopropyl]-ethyl}-O-methyl-hydroxylamine as a mixture of diastereomeres in form of a clear viscous oil.

¹H NMR (CDCl₃, 400 MHz): 0.88-1.18 (4m, 2H); 1.21+1.31 (2d, 3H); 1.35-1.44 (m, 1H); 1.71-1.87 (2m, 1H); 2.47-2.61 (2m, 1H); 3.57+3.59 (2s; 3H); 5.5-6.0 (b, 1H); 6.86-6.92 (t, 1H); 7.03-7.10 (m, 1H); 7.13-7.15 (d, 1H).

MS [M+H]⁺: 244/246.

Example P15

Preparation of trans-N-{1-[2-(2,6-dichlorophenyl)-cyclopropyl]-ethyl}-O-methyl-hydroxylamine

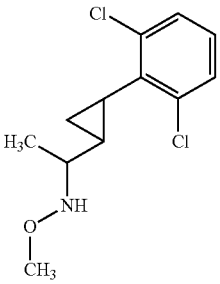 [SMILES: CONC(C)C1CC1c1c(Cl)cccc1Cl]

A solution of 1-[2-(2,6-dichloro-phenyl)-cyclopropyl]-ethanone O-methyl-oxime (300 mg, 1.16 mmol), prepared as described in example P22, in ethanol (2 ml) and acetic acid (1 ml) was treated at ambient temperature with sodium cyanoborohydride (144 mg, 2.32 mmol) added in one portion. The resulting solution was stirred at ambient temperature for 10 hours. The solvent was evaporated under reduced pressure (co-evaporation with toluene twice) and the residue was slurried with 1 M NaOH (15 ml). The aqueous phase was extracted with ether (3×10 ml), washed with brine and dried over anhydrous Na₂SO₄. After removal of the solvent, the residue was purified by flash chromatography over silica gel (15 g) (eluent: c-hexane/ethyl acetate 3:1). 260 mg (89.0% of theory) of trans-N-{1-[2-(2,6-dichlorophenyl)-cyclopropyl]-ethyl}-O-methyl-hydroxylamine as a mixture of diastereomeres was obtained in form of a clear liquid.

¹H NMR: (CDCl₃, 400 MHz): 0.82-1.53 (m, 3H); 1.16-1.19+1.38-1.42 (2d, 3H); 1.71-1.79 (m, 1H); 2.52-2.63+2.80-2.90 (2m, 1H); 3.58+3.59 (2s, 3H); 5.78 (s_br,1H); 7.03-7.11 (m, 1H); 7.28-7.29 (m, 2H).

MS [M+H]⁺260/262/264.

Example P16

Preparation of trans-N-{1-[2-(2,4,6-trichlorophenyl)-cyclopropyl]-ethyl}-O-methyl-hydroxylamine

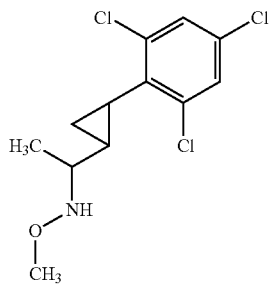 [SMILES: CONC(C)C1CC1c1c(Cl)cc(Cl)cc1Cl]

A solution of 1-[2-(2,4,6-trichloro-phenyl)-cyclopropyl]-ethanone O-methyl-oxime (0.19 mmol), prepared as described in example P23, in ethanol (1 ml) and acetic acid (1 ml) was treated at ambient temperature with sodium cyanoborohydride (200 mg, 3.18 mmol) added in one portion.

The resulting solution was stirred at ambient temperature for 20 hours. The solvent was evaporated under reduced pressure (co-evaporation with toluene twice) and the residue was slurried with 1 M NaOH (5 ml). The aqueous phase was extracted with ether (3×10 ml), washed with brine and dried over anhydrous $Na_2SO_4$. After removal of the solvent, the residue was purified by flash chromatography over silica gel (5 g) (eluent: c-hexane/ethyl acetate 5:1). 25 mg (45.0% of theory) of trans-N-{1-[2-(2,4,6-trichlorophenyl)-cyclopropyl]-ethyl}-O-methyl-hydroxylamine as a mixture of diastereomeres was obtained in form of a clear liquid.

$^1$H NMR: ($CDCl_3$, 400 MHz): 0.81-1.48 (m, 3H); 1.17-1.20+1.39-1.42 (2d, 3H); 1.65-1.75 (m, 1H); 2.52-2.63+2.80-2.90 (2m, 1H); 3.58+3.59 (2s, 3H); 5.75 ($s_{br}$,1H); 7.28-7.29 (m, 2H).

MS [M+H]$^+$294/296/298.

Example P17

Preparation of trans O-methyl-N-{1-[2-(2,4,5-trichloro-thiophen-3-yl)-cyclopropyl]-ethyl}-hydroxylamine

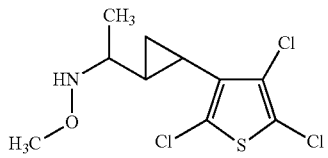

To a stirred solution of trans 1-[2-(2,4,5-trichloro-thiophen-3-yl)cyclopropyl]-ethanone O-methyl-oxime (2.85 g; 9.5 mmol) prepared as described in example P24, in acetic acid (20 ml) at ambient temperature was added portionwise sodium cyanoborohydride (1.80 g; 29 mmol). The reaction mixture was stirred for 50 hours at ambient temperature then poured on sodium hydroxide solution (0.5M; 150 ml) and extracted with dichloromethane (3×50 ml). Combined organic layers were washed with sodium hydroxide solution (0.5M; 100 ml) and dried over anhydrous sodium sulphate. The solvent was removed in vacuo and the residue was purified by flash chromatography over silica gel (elution gradient: cyclohexane/ethyl acetate 99:1 to 80:20) to afford 1.78 g (62% of theory) of trans O-methyl-N-{1-[2-(2,4,5-trichloro-thiophen-3-yl)-cyclopropyl]-ethyl}-hydroxylamine as a mixture of diastereomeres in form of a yellow oil.

$^1$H NMR ($CDCl_3$, 400 MHz): 0.83-1.17 (4m, 2H); 1.19+1.33 (2d, 3H); 1.36-1.44 (m, 1H); 1.52-1.58 (2m; 1H); 2.42-2.59 (2m, 1H); 3.57+3.58 (2s, 3H); 5.5-6.0 ($s_{br}$,1H).

MS [M+H]$^+$300/302/304.

Example P18

Preparation of trans N-{1-[2-(5-chloro-thiophen-2-yl)-cyclopropyl]-ethyl}-O-methyl-hydroxylamine

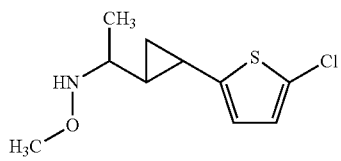

To a stirred solution of trans 1-[2-(5-Chloro-thiophen-2-yl)cyclopropyl]-ethanone O-methyl-oxime (1.2 g; 5.2 mmol) prepared as described in example P25, in acetic acid (15 ml) at ambient temperature was added portionwise sodium cyanoborohydride (1.0 g; 15.7 mmol). The reaction mixture was stirred for 16 hours at ambient temperature then poured on sodium hydroxide solution (0.5M; 150 ml) and extracted with dichloromethane (3×50 ml). Combined organic layers were dried over anhydrous sodium sulphate. The solvent was removed in vacuo and the residue was purified by flash chromatography over silica gel (elution gradient: cyclohexane/ethyl acetate 99:1 to 50:50) to afford 0.91 g (79% of theory) of trans N-{1-[2-(5-chloro-thiophen-2-yl)-cyclopropyl]-ethyl}-O-methyl-hydroxylamine as a mixture of diastereomeres in form of a clear viscous oil.

$^1$H NMR ($CDCl_3$, 400 MHz): 0.79-1.02 (4m, 2H); 1.07-1.16 (m, 1H); 1.15+1.22 (2d, 3H); 1.79-2.00 (2m, 1H); 2.41-2.48 (m, 1H); 3.56+3.57 (2s; 3H); 4.8-5.7 (b, 1H); 6.50 (d, 1H); 6.67 (d, 1H).

Example P19

Preparation of trans 1-[2-(2-chloro-phenyl)-cyclopropyl]-ethanone O-methyl-oxime

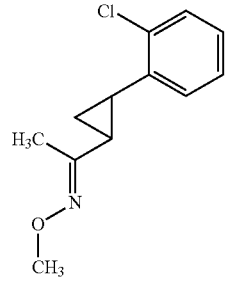

To a stirred solution of trans 1-[2-(2-chloro-phenyl)-cyclopropyl]-ethanone (1.0 g; 5.1 mmol) in methanol (10 ml) at ambient temperature was added pyridine (0.85 ml; 10 mmol) and methoxyamine hydrochloride (0.86 g; 10 mmol). The reaction mixture was stirred for 16 hours at ambient temperature then poured in water (50 mL) and extracted with dichloromethane (3×30 ml). Combined organic layers were dried over anhydrous sodium sulphate. The solvent was removed in vacuo to afford 1.1 g (98% of theory) of trans 1-[2-(2-chloro-phenyl)-cyclopropyl]-ethanone O-methyl-oxime as an oil.

$^1$H NMR ($CDCl_3$, 400 MHz): 1.17-1.50 (4m, 2H); 1.73+1.83 (2s, 3H); 1.73-1.79 (m, 1H); 2.42-2.61 (2m, 1H); 3.85 (s; 3H); 6.99-7.36 (m, 4H).

Example P20

Preparation of 1-[2-(2,4-dichloro-phenyl)-cyclopropyl]-ethanone O-methyl-oxime

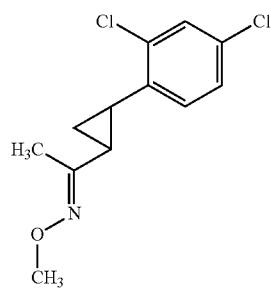 [SMILES: CO/N=C(\C)C1CC1c1ccc(Cl)cc1Cl]

A solution of trans 1-[2-(2,4-dichloro-phenyl)-cyclopropyl]-ethanone (0.24 g, 1.05 mmole) prepared as described in example P26, in THF (1.5 ml) and water (3.0 ml) was treated with O-methyl hydroxylamine hydrochloride (0.15 g, 1.79 mmol) followed by sodium acetate (125 mg, 1.52 mmol). The resulting solution was stirred at ambient temperature over night for 16 hours. The reaction mixture was diluted with ethylacetate (20 ml), washed with brine (50 ml) and dried over anhydrous $Na_2SO_4$. After removal of the solvent the residue was purified by flash chromatography over silica gel (15 g) (eluent: n-hexane/ethyl acetate 20:1) to afford 0.20 g (74% of theory) of 1-[2-(2,4-dichloro-phenyl)-cyclopropyl]-ethanone O-methyl-oxime as an E/Z mixture in form of an oil.

$^1$H NMR ($CDCl_3$, 400 MHz): 1.23-1.31 (m, 1H); 1.33-1.42 (m, 1H); 1.73 (2s, 3H); 2.43-2.58 (m, 2H); 3.85 (2s, 3H); 6.98-7.02 (dd, 1H); 7.16-7.19 (dd, 1H); 7.34-7.35 (dd, 1H).
MS [M+H]$^+$ 258/260/262.

Example P21

Preparation of trans 1-[2-(2-chloro-6-fluoro-phenyl)-cyclopropyl]-ethanone O-methyl-oxime

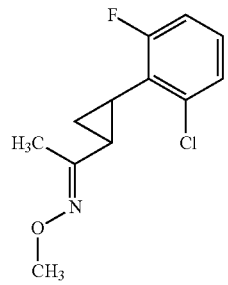 [SMILES: CO/N=C(\C)C1CC1c1c(F)cccc1Cl]

To a stirred solution of trans 1-[2-(2-Chloro-6-fluoro-phenyl)-cyclopropyl]-ethanone (1.0 g; 4.7 mmol) in methanol (10 ml) at ambient temperature was added pyridine (0.60 ml; 7.0 mmol) and methoxyamine hydrochloride (0.60 g; 7.0 mmol). The reaction mixture was stirred for 16 hours at ambient temperature then poured in water (50 ml) and extracted with dichloromethane (3×30 ml). Combined organic layers were dried over anhydrous sodium sulphate. The solvent was removed in vacuo to afford 1.1 g (100% of theory) of trans 1-[2-(2-Chloro-6-fluoro-phenyl)-cyclopropyl]-ethanone O-methyl-oxime as an E/Z mixture in form of an oil.

$^1$H NMR ($CDCl_3$, 400 MHz): 1.32-1.59 (4m, 2H); 1.72+1.85 (2s, 3H); 1.95-2.75 (4m, 2H); 3.85+3.86 (2s; 3H); 6.89-6.94 (m, 1H); 7.07-7.17 (2m, 2H).

Example P22

Preparation of 1-[2-(2,6-dichloro-phenyl)-cyclopropyl]-ethanone O-methyl-oxime

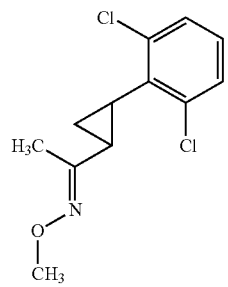 [SMILES: CO/N=C(\C)C1CC1c1c(Cl)cccc1Cl]

A solution of trans 1-[2-(2,6-dichloro-phenyl)-cyclopropyl]-ethyanone (0.35 g, 1.53 mmole) prepared as described in example P27 in THF (5 ml) and water (1.0 ml) was treated with 0-methyl hydroxylamine hydrochloride (0.22 g, 2.60 mmol) followed by sodium acetate (182 mg, 2.22 mmol). The resulting solution was stirred at ambient temperature over night for 16 hours. The reaction mixture was diluted with ethylacetate (20 ml), washed with brine (50 ml) and dried over anhydrous $Na_2SO_4$. After removal of the solvent the residue was purified by flash chromatography over silica gel (20 g) (eluent: n-hexane/ethyl acetate 20:1) to afford 0.30 g (76% of theory) of 1-[2-(2,6-dichloro-phenyl)-cyclopropyl]-ethanone O-methyl-oxime as an E/Z mixture in form of an oil.

MS [M+H]$^+$ 258/260/262.

Example P23

Preparation of 1-[2-(2,4,6-trichloro-phenyl)-cyclopropyl]-ethanone O-methyl-oxime

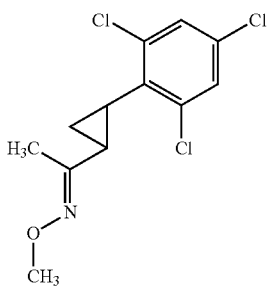 [SMILES: CO/N=C(\C)C1CC1c1c(Cl)cc(Cl)cc1Cl]

A solution of trans 1-[2-(2,4,6-trichloro-phenyl)-cyclopropyl]-ethyanone (50 mg, 0.19 mmole) prepared as described in example P28, in THF (5.0 ml) and water (1.0 ml) was treated with O-methyl hydroxylamine hydrochloride (27 mg, 0.32 mmol) followed by sodium acetate (23 mg, 0.28 mmol). The resulting solution was stirred at ambient temperature over night for 16 hours. The reaction mixture was diluted with ethylacetate (5 ml), washed with brine (10 ml) and dried over anhydrous $Na_2SO_4$. After removal of the solvent crude 1-[2-(2,4,6-trichloro-phenyl)-cyclopropyl]-ethanone O-methyl-oxime was obtained as an E/Z mixture in form of an oil which was used without further purification for the next step.

Example P24

Preparation of trans 1-[2-(2,4,5-trichloro-thiophen-3-yl)-cyclopropyl]-ethanone O-methyl-oxime

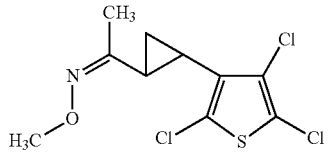 [SMILES: CO/N=C(/C)C1CC1c1c(Cl)sc(Cl)c1Cl]

To a stirred solution of trans 1-[2-(2,4,5-trichloro-thiophen-3-yl)-cyclopropyl]-ethanone (2.7 g; 10 mmol) prepared as described in example P29, in methanol (20 ml) at ambient temperature was added pyridine (1.25 ml; 15 mmol) and methoxyamine hydrochloride (1.3 g; 15 mmol). The reaction mixture was stirred for 4 hours at ambient temperature then poured in water (50 ml) and extracted with dichloromethane (3×30 ml). Combined organic layers were washed with water (30 ml) and dried over anhydrous sodium sulphate. The solvent was removed in vacuo to afford 2.85 g (95% of theory) of trans 1-[2-(2,4,5-trichloro-thiophen-3-yl)-cyclopropyl]-ethanone O-methyl-oxime as an E/Z mixture in form of an orange oil.

$^1$H NMR (CDCl$_3$, 400 MHz): 1.28-1.55 (3m, 2H); 1.69+1.86 (2s, 3H); 1.92-2.75 (3m, 2H); 3.84+3.86 (2s, 3H).

MS [M+H]$^+$ 298/300/302/304.

Example P25

Preparation of trans 1-[2-(5-chloro-thiophen-2-yl)-cyclopropyl]-ethanone O-methyl-oxime

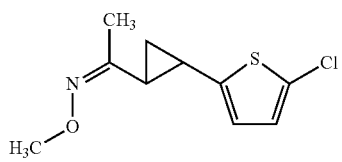

To a stirred solution of trans 1-[2-(5-chloro-thiophen-2-yl)-cyclopropyl]-ethanone (1.0 g; 5.0 mmol) in methanol (10 ml) at ambient temperature was added pyridine (0.85 ml; 10.3 mmol) and methoxyamine hydrochloride (0.86 g; 10.3 mmol). The reaction mixture was stirred for 20 hours at ambient temperature then poured on water (50 ml) and extracted with dichloromethane (3×20 ml). Combined organic layers were dried over anhydrous sodium sulphate. The solvent was removed in vacuo to afford 1.0 g (92% of theory) of trans 1-[2-(5-Chloro-thiophen-2-yl)-cyclopropyl]-ethanone O-methyl-oxime as an E/Z mixture in form of a clear oil.

$^1$H NMR (CDCl$_3$, 400 MHz): 1.11-1.45 (4m, 2H); 1.65+1.78 (2s, 3H); 1.76-2.64 (3m, 2H); 3.82+3.85 (2s; 3H); 3.82+3.85 (2d, 2H).

Example P26

Preparation of trans 1-[2-(2,4-dichloro-phenyl)-cyclopropyl]-ethanone

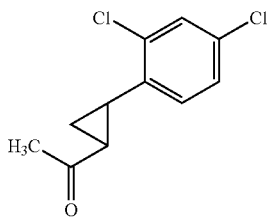

A round bottom flask equipped with magnetic stirrer, nitrogen inlet and additional funnel was charged with trimethyl-sulfoxonium iodide (0.61 g, 2.78 mmol), DMSO (10 ml) and powdered sodium hydroxide (97 mg, 2.44 mmol). The suspension was stirred for 1.0 hour at ambient temperature to yield a solution. So prepared solution was added drop wise at ambient temperature to a solution of (E)-4-(2,4-dichloro-phenyl)-but-3-en-2-one (0.50 g, 2.32 mmol) prepared as described in example P30 in DMSO (10 ml). The reaction mixture was stirred for 0.5 hours, poured onto ice water (100 ml) and extracted with ether (3×25 ml). Combined organic layers were washed with water, brine and dried over anhydrous sodium sulfate. The solvent was removed in vacuo and the residue was purified by flash chromatography over silica gel (25 g) (eluent: n-hexane/ethyl acetate 10:1) to afford 0.33 g (62% of theory) of trans 1-[2-(2,4-dichloro-phenyl)-cyclopropyl]-ethyanone in form of an oil.

$^1$H NMR (CDCl$_3$, 400 MHz): 1.32-1.41 (m, 1H); 1.63-1.74 (m, 1H); 2.01-2.08 (m, 1H); 2.33 (s, 3H); 2.59-2.67 (m, 1H); 6.94-6.98 (dd, 1H); 7.14-7.18 (dd, 1H); 7.37-7.38 (dd, 1H).

MS [M+H]$^+$ 229/231/233

Example P27

Preparation of trans 1-[2-(2,6-dichloro-phenyl)-cyclopropyl]-ethanone

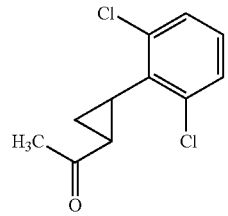

A round bottom flask equipped with magnetic stirrer, nitrogen inlet and additional funnel was charged with trimethyl-sulfoxonium iodide (1.1 g, 5.02 mmol), DMSO (10 ml) and powdered sodium hydroxide (0.175 g, 4.39 mmol). The suspension was stirred for 1.5 hours at ambient temperature to yield a solution. So prepared solution was added drop wise at ambient temperature to a solution of 4-(2,6-dichloro-phenyl)-but-3-en-2-one (0.90 g, 4.18 mmol) prepared as described in example P31 in DMSO (5 ml). The reaction mixture was stirred for 0.5 hours, poured onto ice and extracted with ether (3×25 ml). Combined organic layers were washed with water, brine and dried over anhydrous sodium sulfate. The solvent was removed in vacuo and the residue was purified by flash chromatography over silica gel (25 g) (eluent: n-hexane/ethyl acetate 20:1) to afford 0.30 g (31% of theory) of trans 1-[2-(2,6-dichloro-phenyl)-cyclopropyl]-ethyanone in form of a pale yellow liquid.

$^1$H NMR (CDCl$_3$, 400 MHz): 1.40-1.48 (m, 1H); 1.78-1.86 (m, 1H); 2.21-2.30 (m, 1H); 2.34-2.40 (m, 1H); 2.41 (s, 3H); 7.12-7.18 (m, 1H); 7.28-7.33 (dd, 2H)

MS [M+H]$^+$: 229/231/233

Example P28

Preparation of trans 1-[2-(2,4,6-trichloro-phenyl)-cyclopropyl]-ethanone

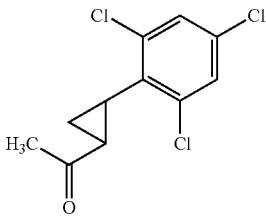

A round bottom flask equipped with magnetic stirrer, nitrogen inlet and additional funnel was charged with trimethylsulfoxonium iodide (106 mg, 0.40 mmol), DMSO (2.5 ml) and powdered sodium hydroxide (0.18 mg, 0.44 mmol). The suspension was stirred for 1.0 hour at ambient temperature to yield a solution. So prepared solution was added drop wise at ambient temperature to a solution of (E)-4-(2,4,6-trichloro-phenyl)-but-3-en-2-one (0.10 g, 0.40 mmol) prepared as described in example P32 in DMSO (2.5 ml). The reaction mixture was stirred for 0.5 hours, poured onto ice water (10 ml) and extracted with ether (3×5 ml). Combined organic layers were washed with water, brine and dried over anhydrous sodium sulfate. The solvent was removed in vacuo and the residue was purified by flash chromatography over silica gel (25 g) (eluent: n-hexane/ethyl acetate 20:1) to afford 60 mg (57% of theory) of trans 1-[2-(2,4,6-trichloro-phenyl)-cyclopropyl]-ethyanone in form of a pale yellow liquid.

$^1$H NMR (CDCl$_3$, 400 MHz): 1.38-1.50 (m, 1H); 1.78-1.84 (m, 1H); 2.18-2.27 (m, 1H); 2.30-2.39 (m, 1H); 2.40+2.41 (2s, 3H); 7.32 (s, 2H).

MS [M+H]$^+$: 263/265/267

Example P29

Preparation of trans-1-[2-(2,4,5-trichloro-thiophen-3-yl)-cyclopropyl]-ethanone

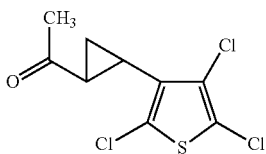

To a stirred mixture of solid sodium hydride (55-65% in oil; 1.5 g; 34 mmol) and trimethylsulfoxonium iodide (7.6 g; 34 mmol) under nitrogen was added in one portion a solution of (E)-4-(2,4,5-Trichloro-thiophen-3-yl)-but-3-en-2-one (7.0 g; 27 mmol) prepared as described in example P33 in dry dimethylsulfoxide (300 mL). The reaction is slightly exothermic and gas evolution is observed. The reaction mixture was stirred for 10 minutes at ambient temperature then poured on water (600 ml) and brine (100 ml) then extracted with dichloromethane (3×300 ml). Combined organic layers were washed with water (2×800 ml) and dried over anhydrous sodium sulphate. The solvent was removed in vacuo and the residue was purified by chromatography over silica gel (eluant: cyclohexane/ethyl acetate 90:10) to afford 2.7 g (37% of theory) of trans-1-[2-(2,4,5-trichloro-thiophen-3-yl)-cyclopropyl]-ethanone as a yellow oil.

$^1$H NMR (CDCl$_3$, 400 MHz): 1.46-1.68 (2m, 2H); 2.19-2.30 (2m, 2H); 2.39 (s, 3H).

Example P30

Preparation of (E)-4-(2,4-dichloro-phenyl)-but-3-en-2-one

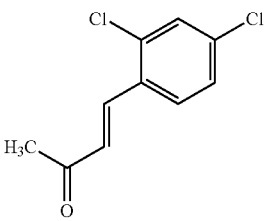

A round bottom flask equipped with magnetic stirrer and nitrogen inlet was charged with 2,4-dichlorobenzaldehyde (1.75 g, 10.0 mmol), acetone (44.1 ml, 0.60 mol) and water (20 ml). The mixture was cooled to 0° C. and a solution of sodium hydroxide (0.44 g, 11.0 mmol) in water (20 ml) was added drop wise during 1 hour to the vigorous stirred suspension. The reaction mixture was stirred for an additional 1.0 hour. The reaction mixture was concentrated in vacuo, poured onto 10% HCl (100 ml) and extracted with ethyl acetate (3×50 ml). Combined organic layers were dried over anhydrous sodium sulfate. The solvent was removed in vacuo and the residue was purified by flash chromatography over silica gel (350 g) (eluent: n-hexane/ethyl acetate 1:1) to afford 1.9 g (88% of theory) of (E)-4-(2,4-dichloro-phenyl)-but-3-en-2-one in form of a pale yellow oil.

$^1$H NMR (CDCl$_3$, 400 MHz): 2.42 (s, 3H); 6.62-6.68 (d, 1H); 7.28-7.31 (dd, 1H); 7.43-7.44 (dd, 2H); 7.55-7.58 (d, 1H); 7.82-7.88 (d, 1H).

MS [M+H]$^+$: 215/217/219

Example P31

Preparation of (E)-4-(2,6-dichloro-phenyl)-but-3-en-2-one

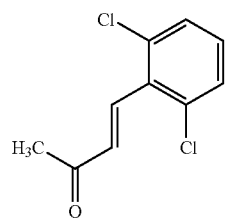

A round bottom flask equipped with magnetic stirrer and nitrogen inlet was charged with 2,6-dichlorobenzaldehyde (5.0 g, 28.57 mmol), acetone (42 ml, 0.571 mol) and water (20 ml). The mixture was cooled to 0° C. and a solution of sodium hydroxide (1.14 g, 28.57 mmol) in water (20 ml) was added drop wise during 1 hour to the vigorous stirred suspension. The reaction mixture was stirred for an additional 0.5 hour. The reaction mixture was concentrated in vacuo, poured onto 10% HCl (100 ml) and extracted with ethyl acetate (3×50 ml).

Combined organic layers were dried over anhydrous sodium sulfate. The solvent was removed in vacuo and the residue was purified by flash chromatography over silica gel (350 g) (eluent: n-hexane/ethyl acetate 10:1) to afford 6.0 g (97% of theory) of (E)-4-(2,6-dichloro-phenyl)-but-3-en-2-one in form of a pale yellow oil.

$^1$H NMR (CDCl$_3$, 400 MHz): 2.43 (s, 3H); 6.78-6.84 (d, 1H); 7.16-7.29 (m, 1H); 7.37-7.41 (d, 2H); 7.58-7.62 (d, 1H).

MS [M+H]$^+$: 215/217/219

Example P32

Preparation of (E)-4-(2,4,6-trichloro-phenyl)-but-3-en-2-one

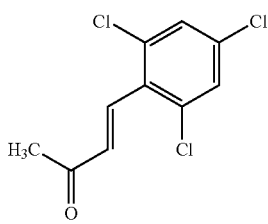

A round bottom flask equipped with magnetic stirrer and nitrogen inlet was charged with but-3-en-2-one (1.14 g, 16.25 mmol), 1,3,5-trichloro-2-iodo-benzene (2.0 g, 6.5 mmol), Pd(OAc)$_2$ (125 mg, 0.65 mmol), sodium hydrogen carbonate (1.64 g, 19.5 mmol) and tetrabutylammonium chloride (2.17 g, 7.8 mmol) in DMF (20 ml). The mixture was stirred at 50° C. for 24 hours. The reaction mixture was poured onto water (100 ml) and extracted with ether (3×50 ml). Combined organic layers were dried over anhydrous sodium sulphate, filtered and concentrated in vacuo. The residue was purified by flash chromatography over silica gel (150 g) (eluent: n-hexane/ethyl acetate 1:20) to afford 1.02 g (63% of theory) of (E)-4-(2,4,6-trichloro-phenyl)-but-3-en-2-one in form of an oil.

MS [M+H]$^+$ 249/251/253

Example P33

Preparation of (E)-4-(2,4,5-trichloro-thiophen-3-yl)-but-3-en-2-one

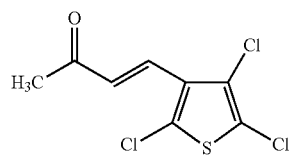

To a stirred solution of 2,4,5-trichloro-thiophene-3-carbaldehyde (10.3 g; 48 mmol) and lithium bromide (0.10 g; 1.2 mmol) in acetonitrile (100 mL) at 15° C. under nitrogen was added acetylmethylene-triphenylphosphorane (15.6 g; 49 mmol). The reaction mixture was stirred for 3 hours at ambient temperature then poured in water (200 ml) and extracted with dichloromethane (3×70 ml). Combined organic layers were dried over anhydrous sodium sulphate. The solvent was removed in vacuo and the residue was purified by chromatography over silica gel (eluant: cyclohexane/ethyl acetate 90:10) to afford 11.2 g (91% of theory) of (E)-4-(2,4,5-trichloro-thiophen-3-yl)-but-3-en-2-one as yellow solid.

$^1$H NMR (CDCl$_3$, 400 MHz):

2.39 (s, 3H); 7.10-7.42 (m, 2H).

Tables 1 to 3: Compounds of Formula Ia:

The invention is further illustrated by the preferred individual compounds of formula (Ia) listed below in Tables 1 to 3. Characterising data are given in Table 5.

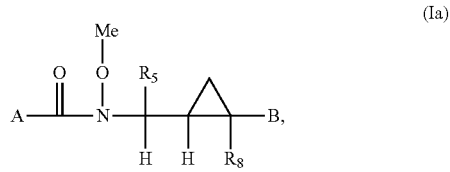
(Ia)

In the compounds of formula Ia, A is selected from the groups consisting of

A$_1$,

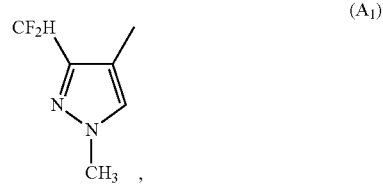
(A$_1$)

A$_2$,

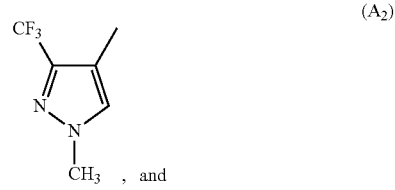
(A$_2$)

A$_3$

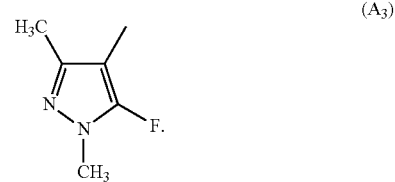
(A$_3$)

B is selected from

B$_1$,

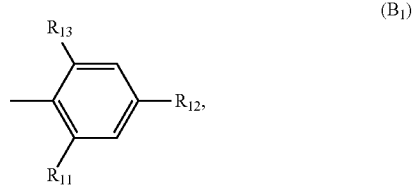
(B$_1$)

B₂

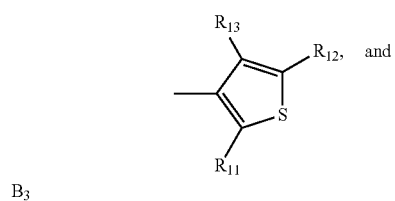

(B₂)

B₃

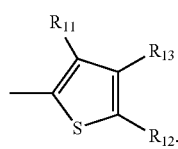

(B₃)

Each of Tables 1 to 3, which follow the Table Y below, comprises 95 compounds of formula (Ia) in which $R_5$, $R_8$, B, $R_{11}$, $R_{12}$ and $R_{13}$ have the values given in Table Y and A has the value given in the relevant Table 1 to 3. Thus Table 1 corresponds to Table Y when Y is 1 and A has the value given under the Table 1 heading, Table 2 corresponds to Table Y when Y is 2 and A has the value given under the Table 2 heading, and so on for Table 3.

TABLE Y ("Me" means the methyl group):

| Cpd No. | $R_5$ | $R_8$ | B | $R_{11}$ | $R_{12}$ | $R_{13}$ |
|---|---|---|---|---|---|---|
| Y.001 | Me | H | B₁ | H | H | H |
| Y.002 | Me | H | B₁ | H | Cl | H |
| Y.003 | Me | H | B₁ | H | Br | H |
| Y.004 | Me | H | B₁ | H | I | H |
| Y.005 | Me | H | B₁ | H | Me | H |
| Y.006 | Me | H | B₁ | H | CF₃ | H |
| Y.007 | Me | H | B₁ | H | C≡CH | H |
| Y.008 | Me | H | B₁ | H | t-Bu | H |
| Y.009 | Me | H | B₁ | H | 4-Cl-phenyl | H |
| Y.010 | Me | H | B₁ | H | 4-Cl-phenoxy | H |
| Y.011 | Me | H | B₁ | Cl | H | H |
| Y.012 | Me | H | B₁ | Br | H | H |
| Y.013 | Me | H | B₁ | I | H | H |
| Y.014 | Me | H | B₁ | CH₃ | H | H |
| Y.015 | Me | H | B₁ | C≡CH | H | H |
| Y.016 | Me | H | B₁ | t-Bu | H | H |
| Y.017 | Me | H | B₁ | F | Cl | H |
| Y.018 | Me | H | B₁ | Cl | Cl | H |
| Y.019 | Me | H | B₁ | Cl | Br | H |
| Y.020 | Me | H | B₁ | Cl | I | H |
| Y.021 | Me | H | B₁ | Cl | Me | H |
| Y.022 | Me | H | B₁ | Cl | CF₃ | H |
| Y.023 | Me | H | B₁ | Cl | C≡CH | H |
| Y.024 | Me | H | B₁ | Cl | t-Bu | H |
| Y.025 | Me | H | B₁ | Cl | 4-Cl-phenyl | H |
| Y.026 | Me | H | B₁ | Cl | 4-Cl-phenoxy | H |
| Y.027 | Me | H | B₁ | F | H | Cl |
| Y.028 | Me | H | B₁ | Cl | H | Cl |
| Y.029 | Me | H | B₁ | Cl | H | Br |
| Y.030 | Me | H | B₁ | Cl | H | I |
| Y.031 | Me | H | B₁ | Cl | H | Me |
| Y.032 | Me | H | B₁ | Cl | H | CF₃ |
| Y.033 | Me | H | B₁ | F | Cl | Cl |
| Y.034 | Me | H | B₁ | Cl | Cl | Cl |
| Y.035 | Me | H | B₁ | Cl | Br | Cl |
| Y.036 | Me | H | B₁ | Cl | I | Cl |
| Y.037 | Me | H | B₁ | Cl | Me | Cl |
| Y.038 | Me | H | B₁ | Cl | CF₃ | Cl |
| Y.039 | Me | H | B₁ | Cl | C≡CH | Cl |
| Y.040 | Me | H | B₁ | Cl | t-Bu | Cl |
| Y.041 | Me | H | B₁ | Cl | 4-Cl-phenyl | Cl |

TABLE Y-continued ("Me" means the methyl group):

| Cpd No. | $R_5$ | $R_8$ | B | $R_{11}$ | $R_{12}$ | $R_{13}$ |
|---|---|---|---|---|---|---|
| Y.042 | Me | H | B₂ | H | H | H |
| Y.043 | Me | H | B₂ | H | Cl | H |
| Y.044 | Me | H | B₂ | H | Br | H |
| Y.045 | Me | H | B₂ | H | I | H |
| Y.046 | Me | H | B₂ | H | Me | H |
| Y.047 | Me | H | B₂ | H | C≡CH | H |
| Y.048 | Me | H | B₂ | H | t-Bu | H |
| Y.049 | Me | H | B₂ | Cl | H | H |
| Y.050 | Me | H | B₂ | Br | H | H |
| Y.051 | Me | H | B₂ | I | H | H |
| Y.052 | Me | H | B₂ | CH₃ | H | H |
| Y.053 | Me | H | B₂ | C≡CH | H | H |
| Y.054 | Me | H | B₂ | t-Bu | H | H |
| Y.055 | Me | H | B₂ | H | H | Cl |
| Y.056 | Me | H | B₂ | H | H | Br |
| Y.057 | Me | H | B₂ | H | H | I |
| Y.058 | Me | H | B₂ | H | H | CH₃ |
| Y.059 | Me | H | B₂ | H | H | C≡CH |
| Y.060 | Me | H | B₂ | H | H | t-Bu |
| Y.061 | Me | H | B₂ | H | Cl | Cl |
| Y.062 | Me | H | B₂ | H | Br | Br |
| Y.063 | Me | H | B₂ | Cl | Cl | Cl |
| Y.064 | Me | H | B₂ | Br | Cl | Cl |
| Y.065 | Me | H | B₂ | Cl | Br | Br |
| Y.066 | Me | H | B₂ | Br | Br | Br |
| Y.067 | Me | H | B₃ | H | H | H |
| Y.068 | Me | H | B₃ | F | H | H |
| Y.069 | Me | H | B₃ | Cl | H | H |
| Y.070 | Me | H | B₃ | H | Cl | H |
| Y.071 | Me | H | B₃ | H | H | Cl |
| Y.072 | Me | H | B₃ | Br | H | H |
| Y.073 | Me | H | B₃ | H | Br | H |
| Y.074 | Me | H | B₃ | H | H | Br |
| Y.075 | Me | H | B₃ | Cl | Cl | H |
| Y.076 | Me | H | B₃ | Cl | H | Cl |
| Y.077 | Me | H | B₃ | H | Cl | Cl |
| Y.078 | Me | H | B₃ | Br | Br | H |
| Y.079 | Me | H | B₃ | Br | H | Br |
| Y.080 | Me | H | B₃ | Cl | Cl | Cl |
| Y.081 | Me | H | B₃ | Br | Br | Br |
| Y.082 | Me | Me | B₁ | Cl | H | H |
| Y.083 | Me | Me | B₁ | H | Cl | H |
| Y.084 | Me | Me | B₁ | Cl | Cl | H |
| Y.085 | Me | Me | B₁ | Cl | Cl | Cl |
| Y.086 | Me | Me | B₂ | H | Cl | Cl |
| Y.087 | Me | Me | B₂ | Cl | Cl | Cl |
| Y.088 | H | H | B₁ | Cl | H | H |
| Y.089 | H | H | B₁ | H | Cl | H |
| Y.090 | H | H | B₁ | Cl | Cl | H |
| Y.091 | H | H | B₁ | Cl | Cl | Cl |
| Y.092 | H | H | B₂ | H | Cl | Cl |
| Y.093 | H | H | B₂ | Cl | Cl | Cl |
| Y.094 | Me | H | B₁ | F | Br | H |
| Y.095 | Me | H | B₁ | F | 4-Cl-phenoxy | H |

Table 1 provides 95 compounds of formula (Ia), wherein A is A₁

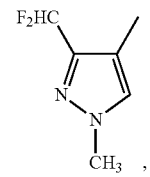

(A₁)

and $R_5$, $R_8$, B, $R_{11}$, $R_{12}$, and $R_{13}$ are as defined in Table Y.

For example, compound 1.034 has the following structure:

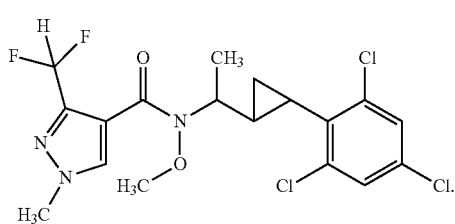
(1.034)

Table 2 provides 95 compounds of formula (Ia), wherein A is $A_2$

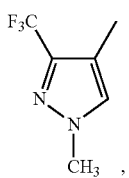
($A_2$)

and $R_5$, $R_8$, B, $R_{11}$, $R_{12}$, and $R_{13}$ are as defined in Table Y.
For example, compound 2.063 has the following structure:

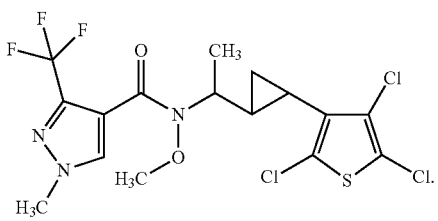
(2.063)

Table 3 provides 95 compounds of formula (Ia), wherein A is $A_3$

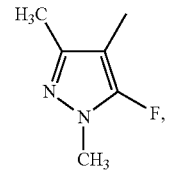
($A_3$)

and $R_5$, $R_8$, B, $R_{11}$, $R_{12}$, and $R_{13}$ are as defined in Table Y.
For example, compound 3.070 has the following structure:

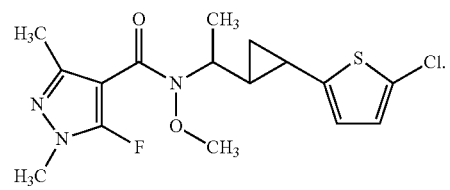
(3.070)

Table 4, which follow the Table Y above, comprises 95 compounds of formula (IIb) in which $R_5$, $R_8$, B, $R_{11}$, $R_{12}$, and $R_{13}$ have the values given in Table Y.

Table 4 provides 95 compounds of formula (IIb)

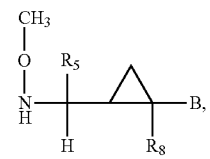
(IIb)

wherein $R_5$, $R_8$, B, $R_{11}$, $R_{12}$, and $R_{13}$ are as defined in Table Y.

TABLE 5

| | Characterising data: | | | |
|---|---|---|---|---|
| Cpd No. | 1H-NMR data: ppm (multiplicity/number of Hs) | diastereomere | MS [M + H]$^+$ | m.p. (° C.) |
| 1.011 | 0.98 – 1.03(m, 1H); 1.12 – 1.17(m, 1H); 1.45 – 1.52(m, 1H); 1.51(d, 3H); 2.23 – 2.28(m, 1H); 3.77(s, 3H); 3.99(s, 3H); 4.07 – 4.16(m, 1H); 6.93 – 6.95(m, 1H); 7.10 – 7.20(m, 2H); 7.10 + 7.24 + 7.38(t, 1H); 7.35 – 7.37(m, 1H); 7.91(s, 1H). | A | 384/386 | oil |
| 1.011 | 1.02 – 1.07(m, 1H); 1.10 – 1.15(m, 1H); 1.44 (d, 3H); 1.48 – 1.55(m, 1H); 2.36 – 2.42(m, 1H); 3.65(s, 3H); 3.96(s, 3H); 4.09 – 4.17(m, 1H); 6.88 – 6.90(m, 1H); 7.06 – 7.17(m, 2H); 7.09 + 7.23 + 7.37(t, 1H); 7.27 – 7.31(m, 1H); 7.86(s, 1H). | B | 384/386 | oil |
| 1.018 | 0.82 – 1.02(m, 2H); 1.12 – 1.59(m, 1H); 1.49 – 1.53(d, 3H); 2.15 – 2.23(m, 1H); 3.78(1s, 3H); 4.00(s; 3H); 4.04 – 4.14(m, 1H); 6.85 – 6.89(d, 1H); 7.04 – 7.43(t, 1H, CHF$_2$); 7.13 – 7.18(dd, 1H); 7.37 – 7.39(d, 1H); 7.91(s, 1H). | A | 418/420/422 | 133-135 |
| 1.018 | 1.02 – 1.14(m, 2H); 1.43 – 1.48(d, 3H); 1.43 – 1.58(m, 1H); 2.28 – 2.37(m, 1H); 3.65(1s, 3H); 3.96(s; 3H); 4.05 – 4.17(m, 1H); 6.79 – 6.83 | B | 418/420/422 | 142-144 |

TABLE 5-continued

Characterising data:

| Cpd No. | 1H-NMR data: ppm (multiplicity/number of Hs) | diastereomere | MS [M + H]+ | m.p. (° C.) |
|---|---|---|---|---|
| | (d, 1H); 7.04 – 7.43(t, 1H, CHF$_2$); 7.12 – 7.16 (dd, 1H); 7.31 – 7.33(d, 1H); 7.95(s, 1H). | | | |
| 1.027 | 0.99 – 1.32(4m, 2H); 1.44 + 1.54(2d, 3H); 1.75 – 2.14(3m, 2H); 3.71 + 3.78(2s, 3H); 3.98 + 3.99(2s, 3H); 4.04 – 4.23(2m, 1H); 6.83 – 6.94(m, 1H); 7.02 – 7.17(m, 2H); 7.10 + 7.24 + 7.38(t, 1H); 7.91 + 7.92(2s, 1H). | mixture | 402/404 | oil |
| 1.028 | 0.81 – 1.68(m, 6H); 1.78 – 2.02(m, 1H); 3.75 + 3.78(2s, 3H); 3.96 + 3.97(2s; 3H); 4.04 – 4.18(m, 1H); 7.03 – 7.18(m, 1H); 7.22 – 7.29(m, 2H); 7.89 + 7.93(2s, 1H). | mixture | 418/420/422 | oil |
| 1.034 | 0.80 – 1.70(m, 6H); 1.72 – 1.95(m, 1H); 3.75 + 3.78(2s, 3H); 3.96 + 3.97(2s; 3H); 4.04 – 4.18 + 4.46 – 4.55(m, 1H); 7.03 – 7.42 + 7.06 – 7.48(2t, 1H, CHF$_2$); 7.24 + 7.26(2s, 2H); 7.89 + 7.93(2s, 1H). | mixture | 452/454/456 | oil |
| 1.063 | 0.94 – 1.35(4m, 2H); 1.44 + 1.57(2d, 3H); 1.68 – 1.95(4m, 2H); 3.73 + 3.78(2s; 3H); 3.99(s, 3H); 3.99 – 4.21(2m, 1H); 7.09 – 7.38(2t, 1H); 7.87 + 7.91(2s, 1H). | mixture | | 110-130 |
| 1.070 | 0.92 – 1.15(4m, 2H); 1.40 + 1.44(2d, 3H); 1.43 – 1.52(m, 1H); 1.95 – 2.15(2m, 1H); 3.71 + 3.77(2s, 3H); 3.99(s, 3H); 3.95 – 4.07(m, 1H); 6.48 + 6.53(2d, 1H); 6.64 + 6.69(2d, 1H); 7.08 + 7.22 + 7.36(2t, 1H); 7.90(s, 1H). | mixture | 390/392 | resin |
| 1.094 | 0.96 – 1.19(2m, 2H), 1.40 – 1.48 (2d, J = 7.0 Hz, 3H), 1.48 – 1.57(m, 1H), 1.95 – 2.21(2m, 1H), 3.61 – 3.77(2s, 3H), 3.95 – 4.00(2s, 3H), 4.00 – 4.11(m, 1H), 6.74 – 6.86(m, 1H), 7.06 – 7.39(m, 3H), 7.84 – 7.92(2s, 1H) | mixture of two | 446/448 | oil |
| 1.095 | 0.96 – 1.26(2m, 2H), 1.42 – 1.51(2d, J = 6.8 Hz, 3H), 1.51 – 1.65(m, 1H), 2.05 – 2.30(2m, 1H), 3.63 – 3.82(2s, 3H), 3.95 – 4.02(2s, 3H), 4.03 – 4.13(m, 1H), 6.91 – 7.05(m, 1H), 7.08 – 7.28(m, 3H), 7.35 – 7.51(m, 4H), 7.84 – 7.94(2s, 1H) | mixture of two | 478/480 | oil |
| 2.063 | 0.94 – 1.38(4m, 2H); 1.42 + 1.57(2d, 3H); 1.66 – 1.98(3m, 2H); 3.63 + 3.67(2s, 3H); 3.99(s, 3H); 4.09 – 4.15(m, 1H); 7.82 + 7.83(2s, 1H). | mixture | 476/478/480 | resin |
| 2.070 | 0.92 – 1.15(4m, 2H); 1.40 + 1.44(2d, 3H); 1.45 – 1.52(m, 1H); 1.94 – 2.17(2m, 1H); 3.60 + 3.66(2s, 3H); 3.98(s, 3H); 3.91 – 4.03(m, 1H); 6.49 + 6.53(2d, 1H); 6.66 + 6.69(2d, 1H); 7.82(s, 1H). | mixture | 408/410 | resin |

Table 5 shows selected melting point and selected NMR data for compounds of Table 1 to 3. CDCl$_3$ is used as the solvent for NMR measurements, unless otherwise stated. If a mixture of solvents is present, this is indicated as, for example: CDCl$_3$/d$_6$-DMSO). No attempt is made to list all characterising data in all cases.

In Table 5 and throughout the description that follows, temperatures are given in degrees Celsius; "NMR" means nuclear magnetic resonance spectrum; MS stands for mass spectrum; "%" is percent by weight, unless corresponding concentrations are indicated in other units.

The following abbreviations are used throughout this description:

m.p. = melting point b.p. = boiling point.

S = singlet br = broad d = doublet dd = doublet of doublets t = triplet q = quartet m = multiplet ppm = parts per million Formulation examples for compounds of formula I:

Example F-1.1 to F-1.2

Emulsifiable Concentrates

| Components | F-1.1 | F-1.2 |
|---|---|---|
| compound of Tables 1-3 | 25% | 50% |
| calcium dodecylbenzenesulfonate | 5% | 6% |
| castor oil polyethylene glycol ether (36 mol ethylenoxy units) | 5% | — |
| tributylphenolpolyethylene glycol ether (30 mol ethylenoxy units) | — | 4% |
| cyclohexanone | — | 20% |
| xylene mixture | 65% | 20% |

Emulsions of any desired concentration can be prepared by diluting such concentrates with water.

Example F-2

Emulsifiable Concentrate

| Components | F-2 |
|---|---|
| compound of Tables 1-3 | 10% |
| octylphenolpolyethylene glycol ether (4 to 5 mol ethylenoxy units) | 3% |
| calcium dodecylbenzenesulfonate | 3% |
| castor oil polyglycol ether (36 mol ethylenoxy units) | 4% |
| cyclohexanone | 30% |
| xylene mixture | 50% |

Emulsions of any desired concentration can be prepared by diluting such concentrates with water.

Examples F-3.1 to F-3.4

Solutions

| Components | F-3.1 | F-3.2 | F-3.3 | F-3.4 |
|---|---|---|---|---|
| compound of Tables 1-3 | 80% | 10% | 5% | 95% |
| propylene glycol monomethyl ether | 20% | — | — | — |
| polyethylene glycol (relative molecular mass: 400 atomic mass units) | — | 70% | — | — |
| N-methylpyrrolid-2-one | — | 20% | — | — |
| epoxidised coconut oil | — | — | 1% | 5% |
| benzin (boiling range: 160-190°) | — | — | — | 94% |

The solutions are suitable for use in the form of microdrops.

Examples F-4.1 to F-4.4

Granulates

| Components | F-4.1 | F-4.2 | F-4.3 | F-4.4 |
|---|---|---|---|---|
| compound of Tables 1-3 | 5% | 10% | 8% | 21% |
| kaolin | 94% | — | 79% | 54% |
| highly dispersed silicic acid | 1% | — | 13% | 7% |
| attapulgite | — | 90% | — | 18% |

The novel compound is dissolved in dichloromethane, the solution is sprayed onto the carrier and the solvent is then removed by distillation under vacuum.

Examples F-5.1 and F-5.2

Dusts

| Components | F-5.1 | F-5.2 |
|---|---|---|
| compound of Tables 1-3 | 2% | 5% |
| highly dispersed silicic acid | 1% | 5% |
| talcum | 97% | — |
| kaolin | — | 90% |

Ready for use dusts are obtained by intimately mixing all components.

Examples F-6.1 to F-6.3

Wettable Powders

| Components | F-6.1 | F-6.2 | F-6.3 |
|---|---|---|---|
| compound of Tables 1-3 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7 to 8 mol ethylenoxy units) | — | 2% | — |
| highly dispersed silicic acid | 5% | 10% | 10% |
| kaolin | 62% | 27% | — |

All components are mixed and the mixture is thoroughly ground in a suitable mill to give wettable powders which can be diluted with water to suspensions of any desired concentration.

Example F7

Flowable Concentrate for Seed Treatment

| | |
|---|---|
| compound of Tables 1-3 | 40% |
| propylene glycol | 5% |
| copolymer butanol PO/EO | 2% |

| | |
|---|---|
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

BIOLOGICAL EXAMPLES

Fungicidal Action

Example B-1

Action Against *Botrytis cinerea*—Fungal Growth Assay

Conidia of the fungus from cryogenic storage was directly mixed into nutrient broth (PDB potato dextrose broth). After placing a (DMSO) solution of the test compounds (0.002% active ingredient) into a microtiter plate (96-well format) the nutrient broth containing the fungal spores was added. The test plates were incubated at 24° C. and the inhibition of growth was measured photometrically after 3-4 days. The activity of a compound was expressed as fungal growth inhibition (0=no growth inhibition, ratings of 80% to 99% mean good to very good inhibition, 100%=complete inhibition).

Compounds 1.011A, 1.011B, 1.018A, 1.018B, 1.027, 1.028, 1.034, 1.094 and 1.095 show very good activity in this test ($\geq$80% inhibition).

Example B-2

Action Against *Mycosphaerella arachidis* (Early Leaf Spot of Groundnut; *Cercospora arachidicola* [Anamorph]—Fungal Growth Assay Conidia of the fungus from cryogenic storage were directly mixed into nutrient broth (PDB potato dextrose broth). After placing a (DMSO) solution of the test compounds (0.002% active ingredient) into a microtiter plate (96-well format) the nutrient broth containing the fungal spores was added. The test plates were incubated at 24° C. and the inhibition of growth was measured photometrically after 6-7 days. The activity of a compound was expressed as fungal growth inhibition (0=no growth inhibition, ratings of 80% to 99% mean good to very good inhibition, 100%=complete inhibition).

Compounds 1.011A, 1.011B, 1.018A, 1.018B, 1.027, 1.028, 1.034, 1.094 and 1.095 show very good activity in this test ($\geq$80% inhibition).

Example B-3

Action Against *Septoria tritici*—Fungal Growth Assay

Conidia of the fungus from cryogenic storage were directly mixed into nutrient broth (PDB potato dextrose broth). After placing a (DMSO) solution of the test compounds (0.002% active ingredient) into a microtiter plate (96-well format) the nutrient broth containing the fungal spores was added. The test plates were incubated at 24° C. and the inhibition of growth was determined photometrically after 72 hrs. The activity of a compound was expressed as fungal growth inhibition (0=no growth inhibition, ratings of 80% to 99% mean good to very good inhibition, 100%=complete inhibition).

Compounds 1.011A, 1.011B, 1.018A, 1.018B, 1.027, 1.028, 1.034, 1.094 and 1.095 show very good activity in this test ($\geq$80% inhibition).

Example B-4

Action Against *Monographella nivalis* (Anamorph: *Fusarium nivale*, *Microdochium nivale*; Snow Mould)—Fungal Growth Assay Conidia of the fungus from cryogenic storage were directly mixed into nutrient broth (PDB potato dextrose broth). After placing a DMSO-solution of the test compounds (0.002% active ingredient) into a microtiter plate (96-well format) the nutrient broth containing the fungal spores was added. The test plates were incubated at 24° C. and the inhibition of growth was measured photometrically after 72 hrs (0=no growth inhibition, ratings of 80% to 99% mean good to very good inhibition, 100%=complete inhibition).

Compounds 1.011A, 1.011B, 1.018A, 1.018B, 1.027, 1.028, 1.034, 1.094 and 1.095 show very good activity in this test ($\geq$80% inhibition).

Example B-5

Action Against *Erysiphe graminis* f.sp. *tritici* (Wheat Powdery Mildew)

Wheat leaf segments were placed on agar in multiwell plates (24-well format) and sprayed with test solutions (0.02% active ingredient). After drying, the leaf disks were inoculated with a spore suspension of the fungus. After appropriate incubation the activity of a compound was assessed 7 days after inoculation as preventive fungicidal activity.

Compounds 1.011A, 1.011B, 1.018A, 1.018B, 1.027, 1.028, 1.034, 1.094 and 1.095 show very good activity in this test ($\geq$80% inhibition).

Example B-6

Protective Action Against *Puccinia recondita* (Brown Rust) on Wheat

Wheat leaf segments were placed on agar in multiwell plates (24-well format) and sprayed with test solutions (0.02% active ingredient). After drying, the leaf disks were inoculated with a spore suspension of the fungus. After appropriate incubation the activity of a compound was assessed 8 days after inoculation as preventive fungicidal activity.

Compounds 1.011A, 1.011B, 1.018A, 1.018B, 1.027, 1.028, 1.034, 1.094 and 1.095 show very good activity in this test ($\geq$80% inhibition).

Example B-7

Curative Action Against *Puccinia recondita* (Brown Rust) on Wheat

Wheat leaf segments were placed on agar in multiwell plates (24-well format) and inoculated with a spore suspension of the fungus. One day after inoculation the leaf segments were sprayed with test solutions (0.02% active ingredient). After appropriate incubation the activity of a compound was assessed 8 days after inoculation as curative fungicidal activity.

Compounds 1.018B, 1.027, 1.028, 1.034, 1.094 and 1.095 show very good activity in this test (≧80% inhibition).

Example B-8

Action Against *Pyrenophora teres* (Net Blotch) on Barley

Barley leaf segments were placed on agar in multiwell plates (24-well format) and sprayed with test solutions (0.02% active ingredient). After drying, the leaf disks were inoculated with a spore suspension of the fungus. After appropriate incubation the activity of a compound was assessed 4 days after inoculation as preventive fungicidal activity.

Compounds 1.011A, 1.011B, 1.018A, 1.018B, 1.027, 1.028, 1.034, 1.094 and 1.095 show very good activity in this test (≧80% inhibition).

Example B-9

Action Against *Rhizoctonia solani*—Fungal Growth Assay

Mycelial fragments of a newly grown liquid culture of the fungus were directly mixed into nutrient broth (PDB potato dextrose broth). After placing a (DMSO) solution of the test compounds (0.002% active ingredient) into a microtiter plate (96-well format) the nutrient broth containing the fungal spores was added. The test plates were incubated at 24° C. and the inhibition of growth was measured photometrically after 3-4 days. The activity of a compound was expressed as fungal growth inhibition (0=no growth inhibition, ratings of 80% to 99% mean good to very good inhibition, 100%=complete inhibition).

Compounds 1.028, 1.034, 1.094 and 1.095 show very good activity in this test (≧80% inhibition).

What is claimed is:
1. A compound of formula I

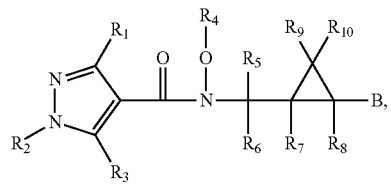

wherein
$R_1$ is $C_1$-$C_4$alkyl or $C_1$-$C_4$haloalkyl;
$R_2$ is $C_1$-$C_4$alkyl;
$R_3$ is hydrogen or halogen;
$R_4$ is hydrogen, $C_1$-$C_4$alkyl or $C_1$-$C_4$halogenalkyl;
$R_5$ and $R_6$ are, independently from each other, hydrogen, halogen, $C_1$-$C_4$alkyl or $C_1$-$C_4$haloalkyl;
$R_7$, $R_8$, $R_9$ and $R_{10}$ are, independently from each other, hydrogen, halogen, $C_1$-$C_6$alkyl, $C_2$-$C_6$alkenyl, $C_3$-$C_6$alkinyl or $C_1$-$C_4$alkoxy;
B is a phenyl or thienyl group, which groups are substituted by $R_{11}$, $R_{12}$ and $R_{13}$;

$R_{11}$, $R_{12}$ and $R_{13}$ are, independently from each other, hydrogen, halogen, $C_1$-$C_6$alkyl, $C_3$-$C_6$alkinyl, $C_1$-$C_4$alkoxy, $C_3$-$C_6$cycloalkyl-$C_3$-$C_6$alkinyl, halophenoxy, halophenyl-$C_3$-$C_6$alkinyl, $C_1$-$C_6$haloalkyl, $C_1$-$C_6$haloalkoxy, or $C_2$-$C_6$haloalkenyloxy; and agrochemically acceptable salts/stereoisomers/diastereoisomers/enantiomers/tautomers and N-oxides of those compounds.

2. A compound of formula I according to claim 1, wherein B is $B_1$

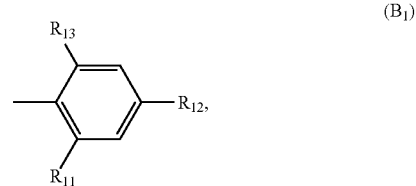

wherein
$R_{11}$, $R_{12}$ and $R_{13}$ are, independently from each other, hydrogen, halogen or $C_1$-$C_6$alkyl;
or B is $B_2$

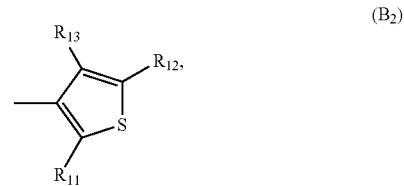

wherein
$R_{11}$, $R_{12}$ and $R_{13}$ are, independently from each other, hydrogen, halogen or $C_1$-$C_6$alkyl;
or B is $B_3$

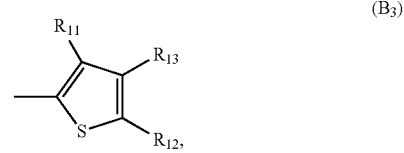

wherein
$R_{11}$, $R_{12}$ and $R_{13}$ are, independently from each other, hydrogen, halogen or $C_1$-$C_6$alkyl.

3. A compound of formula I according to claim 2, wherein B is $B_1$.

4. A compound of formula I according to claim 2, wherein B is $B_2$.

5. A compound of formula I according to claim 2, wherein B is $B_3$.

6. A compound of formula I according to claim 1, wherein
$R_1$ is $C_1$-$C_4$haloalkyl;
$R_2$ is $C_1$-$C_4$ alkyl;
$R_3$ is hydrogen;
$R_4$ is $C_1$-$C_4$alkyl;
$R_5$ is hydrogen or $C_1$-$C_4$alkyl;
$R_6$ is hydrogen;
$R_7$ is hydrogen, $C_1$-$C_4$alkyl or halogen;
$R_8$ is hydrogen, $C_1$-$C_4$alkyl or halogen;

$R_9$ is hydrogen, $C_1$-$C_4$alkyl or halogen;
$R_{10}$ is hydrogen, $C_1$-$C_4$alkyl or halogen;
$R_{11}$, $R_{12}$ and $R_{13}$ are, independently from each other, hydrogen or halogen.

7. A compound of formula I according to claim 6, wherein $R_5$ is methyl.

8. A compound of formula I according to claim 1, wherein
$R_1$ is difluoromethyl;
$R_2$ is methyl;
$R_3$ is hydrogen;
$R_4$ is methyl;
$R_5$ is hydrogen or methyl;
$R_6$ is hydrogen;
$R_7$ is hydrogen, methoxy or chloro; and
$R_8$, $R_9$ and $R_{10}$ are hydrogen.

9. A compound of formula I according to claim 1, wherein
$R_1$ is difluoromethyl or trifluoromethyl;
$R_2$ is methyl;
$R_3$ is hydrogen;
$R_4$ is methyl;
$R_5$ is hydrogen, methyl or ethyl; and
$R_6$, $R_7$, $R_8$, $R_9$ and $R_{10}$ are hydrogen.

10. A compound of formula I according to claim 1, wherein
$R_1$ is $C_1$-$C_4$haloalkyl;
$R_2$ is $C_1$-$C_4$alkyl;
$R_3$ is hydrogen;
$R_4$ is $C_1$-$C_4$alkyl;
$R_5$ is $C_1$-$C_4$alkyl;
$R_6$, $R_7$, $R_8$, $R_9$ and $R_{10}$ are hydrogen;
B is a phenyl or thienyl group, which groups are substituted by $R_{11}$, $R_{12}$ and $R_{13}$; and
$R_{11}$, $R_{12}$ and $R_{13}$ are, independently from each other, hydrogen or halogen.

11. A method of controlling infestation of useful plants by phytopathogenic microorganisms, wherein a compound of formula I according to claim 1 or a composition, comprising this compound as active ingredient, is applied to the plants, to parts thereof or the locus thereof.

12. A composition for controlling phytopathogenic microorganisms, comprising a compound of formula I according to claim 1.

* * * * *